(12) United States Patent
Matsuda et al.

(10) Patent No.: US 8,976,360 B2
(45) Date of Patent: Mar. 10, 2015

(54) SURFACE PLASMON SENSOR AND METHOD OF MEASURING REFRACTIVE INDEX

(75) Inventors: Toyonori Matsuda, Koshi (JP); Hiroyuki Odagawa, Koshi (JP)

(73) Assignee: Institute of National Colleges of Technology, Japan, Tokyo (JP)

( * ) Notice: Subject to any disclaimer, the term of this patent is extended or adjusted under 35 U.S.C. 154(b) by 63 days.

(21) Appl. No.: 13/981,727

(22) PCT Filed: Jan. 26, 2012

(86) PCT No.: PCT/JP2012/051707
§ 371 (c)(1),
(2), (4) Date: Oct. 7, 2013

(87) PCT Pub. No.: WO2012/102350
PCT Pub. Date: Aug. 2, 2012

(65) Prior Publication Data
US 2014/0029006 A1     Jan. 30, 2014

(30) Foreign Application Priority Data
Jan. 26, 2011   (JP) .................................. 2011-014067

(51) Int. Cl.
*G01N 21/55*   (2014.01)
*G01N 21/41*   (2006.01)
(Continued)

(52) U.S. Cl.
CPC ............ *G01N 21/4133* (2013.01); *B82Y 20/00* (2013.01); *G01N 21/41* (2013.01); *G01N 21/553* (2013.01); *G01N 21/55* (2013.01)
USPC ........................................................ 356/445

(58) Field of Classification Search
CPC ... G01N 21/553; G01N 21/55; G01N 21/554; G01N 21/474; G01N 21/57

USPC .......................................................... 356/445
See application file for complete search history.

(56) References Cited

U.S. PATENT DOCUMENTS

| 3,594,064 A | * | 7/1971 | Bierlein et al. | ................ 365/122 |
| 6,219,121 B1 | * | 4/2001 | Sahouani et al. | ............. 349/117 |

(Continued)

FOREIGN PATENT DOCUMENTS

| JP | A-2008-216055 | 9/2008 |
| JP | A-2008-292425 | 12/2008 |
| JP | A-2009-210495 | 9/2009 |

OTHER PUBLICATIONS

May 1, 2012 Written Opinion issued in International Application No. PCT/JP2012/051707 (with translation).
Jun. 27, 2013 International Preliminary Report of Patentability issued in International Application No. PCT/JP2012/051707 (with translation).
Suyama et al., "Surface Plasmon Resonance-absorption on a Metal Grating placed in Conical Mounting," *The Papers of Technical Meeting on Electromagnetic Theory*, EMT 05-6, pp. 29-34, Jan. 2005.

(Continued)

*Primary Examiner* — Tarifur Chowdhury
*Assistant Examiner* — MD Rahman
(74) *Attorney, Agent, or Firm* — Oliff PLC

(57) ABSTRACT

To provide a surface plasmon sensor for measuring a refractive index by which a refractive index can be easily measured with high accuracy without relying on an absorption curve. The surface plasmon sensor includes: a reflection plate which includes a metal layer having a periodic structure and on which a specimen is arranged; a light source which irradiates an incident light to the reflection plate; a light receiving part which receives a reflected light reflected on the reflection plate; and a measurement part which measures a refractive index of the specimen based on phase information on two kinds of waves which are included in reflected light reflected on a periodic structure surface and differ in polarization direction.

10 Claims, 32 Drawing Sheets

(51) Int. Cl.
*B82Y 20/00* (2011.01)
*G01N 21/552* (2014.01)

(56) References Cited

U.S. PATENT DOCUMENTS

| | | | |
|---|---|---|---|
| 6,236,033 B1* | 5/2001 | Ebbesen et al. | 250/216 |
| 6,529,254 B1* | 3/2003 | Suganuma | 349/104 |
| 2009/0279090 A1* | 11/2009 | Wolf et al. | 356/369 |

OTHER PUBLICATIONS

Bai, "Artificial optical activity in chiral resonant nanogratings," *Proceedings of SPIE*, vol. 7393, pp. 73930K-1-73930K-11, 2009.

Suyama et al., "Excitation of surface plasmons on metal grating and its application for refractive index measurement," *The Institute of Electrical Engineers of Japan Kenkyukai Shiryo*, pp. 61-66, Jan. 2007.

May 1, 2012 International Search Report issued in International Patent Application No. PCT/JP2012/051707.

* cited by examiner $$\tan \chi = b/a$$

SURFACE PLASMON SENSOR AND METHOD OF MEASURING REFRACTIVE INDEX

TECHNICAL FIELD

The present invention relates to a surface plasmon sensor, and a method of measuring a refractive index using the surface plasmon sensor.

BACKGROUND ART

As a sensor which optically measures a refractive index of a liquid or the like, there has been known a surface plasmon sensor. In the measurement of an incident angle characteristic (absorption curve) of reflectance ρ when an incident light having a wavelength λ is incident on a surface of metal, the reflectance ρ rapidly decreases at a certain angle of incidence (hereinafter referred to as absorption angle $θ_{sp}$). This phenomenon is called the plasmon resonance absorption, and is a phenomenon which is associated with electromagnetic wave coupling between an incident light and a surface plasmon excited on a surface of metal. As a result of the capture (resonance absorption) of electric power of the incident light into the surface of metal, reflected light intensity decreases.

The surface plasmon sensor is a sensor which measures a refractive index of a specimen such as a liquid by making use of the plasmon resonance absorption. With respect to the surface plasmon sensor, there have been known a surface plasmon sensor where a surface of a prism is coated with a thin metal film and a surface plasmon sensor having the periodic structure where grooves are formed on a surface of metal at equal intervals as disclosed in patent literature 1, for example.

PRIOR ART LITERATURE

Patent Literature

Patent literature 1: JP-A-2008-216055

SUMMARY OF THE INVENTION

Problems that the Invention is to Solve

In using the surface plasmon sensor, an absorption angle $θ_{sp}$ of a reference substance whose refractive index $n_s$ is already known is obtained, and a refractive index n (=$n_s$+Δn) of the specimen is obtained based on the difference $Δθ_{sp}$ (=$θ_{sp}$−$θ'_{sp}$) between an absorption angle $θ'_{sp}$ of a specimen whose refractive index n is measured and the absorption angle $θ_{sp}$ of the reference substance.

As described previously, the absorption angle $θ_{sp}$ is an angle at which the reflectance ρ rapidly decreases and hence, it is necessary to perform the smallest point detection to measure the absorption angle $θ_{sp}$ thus giving rise to a drawback that the measurement of the refractive index n is complicated.

The present invention has been made in view of the above, and it is an object of the present invention to provide a surface plasmon sensor and a method of measuring a refractive index by which a refractive index can be easily measured.

Means for Solving Problems

To overcome the above-mentioned drawback, a surface plasmon sensor according to the present invention is characterized by including: a reflection plate which includes a metal layer having a periodic structure and on which a specimen is arranged; a light source which irradiates an incident light of a p polarized light or an s polarized light to the reflection plate arranged in a conical mount; a light receiving part which receives a reflected light reflected on the reflection plate; and a measurement part which measures a refractive index of the specimen based on a parameter by which ellipticity of the reflected light becomes zero by changing any one of an incident angle of the incident light which the light source irradiates to the reflection plate, an azimuth angle which the plane of incidence makes with respect to the periodic direction of the periodic structure, and a wavelength of the incident light which is incident from the light source as the parameter.

A method of measuring a refractive index according to the present invention is a method of measuring a refractive index using a surface plasmon sensor which measures a refractive index of a specimen arranged on a reflection plate provided with a metal layer having a periodic structure, the method including the steps of: irradiating an incident light of a p polarized light or an s polarized light to the reflection plate arranged in a conical mount from a light source; receiving a reflected light which is reflected on the reflection plate by a light receiving part; measuring a refractive index of the specimen based on a parameter by which ellipticity of the reflected light becomes zero by changing any one of an incident angle of the incident light which the light source irradiates to the reflection plate, an azimuth angle which the plane of incidence makes with respect to the periodic direction of the periodic structure, and a wavelength of the incident light which is incident from the light source as the parameter; and measuring a refractive index of the specimen based on phase information on two kinds of waves which are included in the reflected light received by the light receiving part and differ in polarization direction.

Advantage of the Invention

According to the present invention, the refractive index can be easily measured.

MODE FOR CARRYING OUT THE INVENTION

First Embodiment

Figure 1:
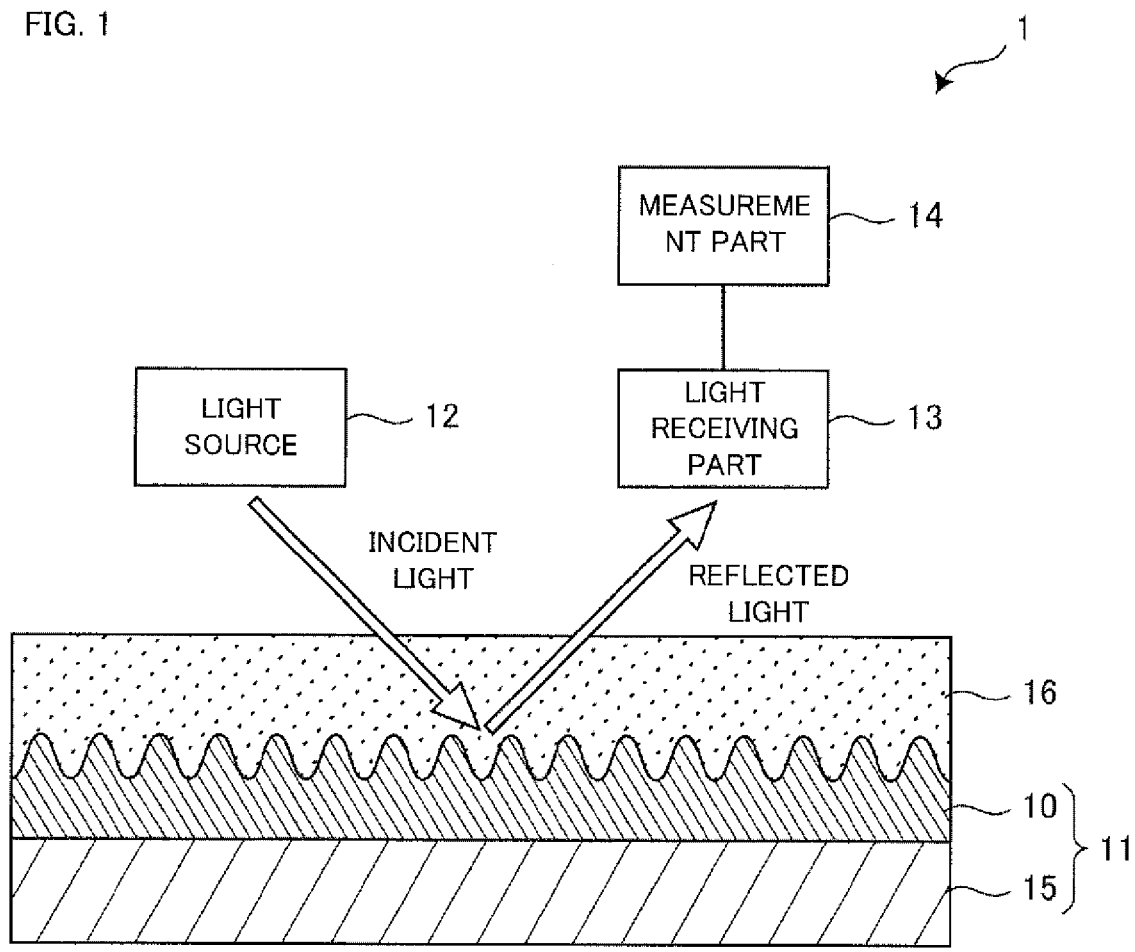
FIG. 1 is a schematic view of a surface plasmon sensor according to a first embodiment of the present invention.

A surface plasmon sensor 1 according to the first embodiment of the present invention is explained. FIG. 1 is a view which showing the schematic constitution of the surface plasmon sensor 1 according to the first embodiment.

The surface plasmon sensor 1 shown in FIG. 1 includes: a reflection plate 11 which includes a metal layer 10 having a periodic structure; a light source 12 which irradiates an incident light onto the reflection plate 11; a light receiving part 13 which receives a reflected light reflected on the reflection plate; and a measurement part 14 which measures a refractive index n of a specimen placed on the reflection plate 11 based on a change in the ellipticity of reflected light.

The respective parts of the surface plasmon sensor 1 are explained in detail.

The reflection plate 11 includes, a substrate 15 made of silicon or the like, for example, and a metal layer 10 made of aluminum or the like which is laminated on a substrate 15, for example.

Figure 2:
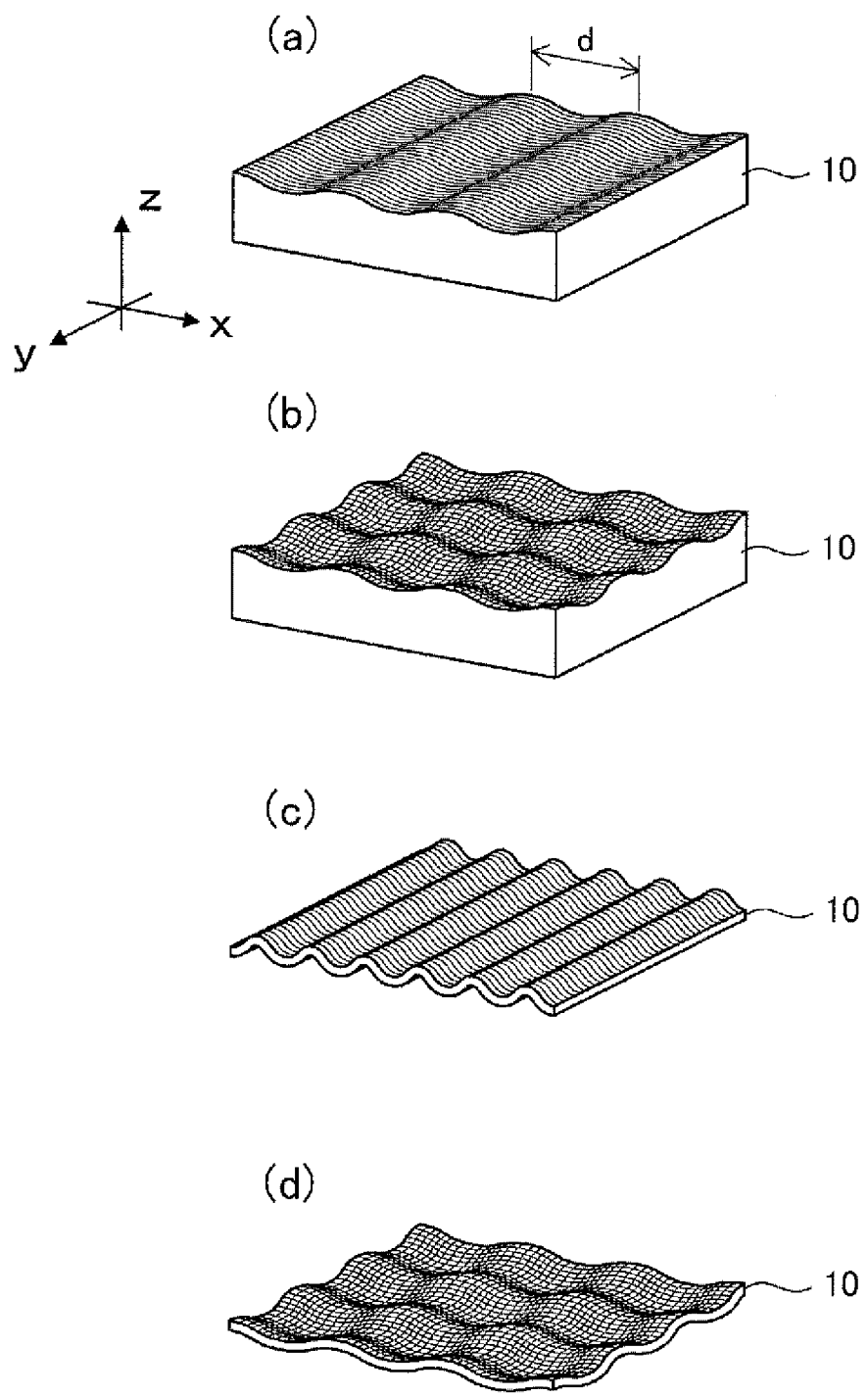
FIG. 2 is a view showing a metal layer according to the first embodiment of the present invention.

FIG. 2 is a view showing one example of the metal layer 10. On a surface of the metal layer 10 which faces a substrate, a corrugated shape is periodically formed at intervals d approximately equal to a wavelength of light. The metal layer 10 has the periodic structure of a period d. The direction that the corrugated shape is repeatedly formed is referred to as the periodic direction.

The periodic structure shown in FIG. 2(a) where the periodic structure is formed on a surface of the metal layer 10 which is not brought into contact with the substrate 15 and the corrugated shape is periodically formed in one direction (x direction in FIG. 2(a)) is referred to as one-dimensional periodic structure. In this case, the periodic direction is constituted of the x direction.

The periodic structure shown in FIG. 2(b) where the periodic structure is formed on a surface of the metal layer 10 which is not brought into contact with the substrate 15 and the corrugated shape is periodically formed in two directions (x, y directions in FIG. 2(b)) is referred to as two-dimensional periodic structure. In this case, the periodic direction is constituted of the x direction and the y direction.

The periodic structure shown in FIG. 2(c) where the metal layer 10 is formed of a metal thin film thinner than the metal layers 10 shown in FIG. 2(a) and FIG. 2(b), for example, having a thickness of several nm to several tens nm, the periodic structure is formed on both surfaces consisting of one surface of the metal layer 10 which is brought into contact with the substrate 15 and the other surface of the metal layer 10 opposite to one surface, and the corrugated shape is periodically formed in one direction (x direction in FIG. 2(c)) is referred to as one-dimensional thin film periodic structure. In this case, the periodic direction is constituted of the x direction.

The periodic structure shown in FIG. 2(d) where the metal layer 10 is formed of a metal thin film thinner than the metal layers 10 shown in FIG. 2(a) and FIG. 2(b), for example, having a thickness of several nm to several tens nm, the periodic structure is formed on both surfaces consisting of one surface of the metal layer 10 which is brought into contact with the substrate 15 and the other surface of the metal layer 10 opposite to one surface, and the corrugated shape is periodically formed in two directions (x, y directions in FIG. 2(d)) is referred to as two-dimensional thin film periodic structure. In this case, the periodic direction is constituted of the x, y directions.

In FIG. 2(c) and FIG. 2(d), although the periodic structure is formed on both surfaces of the metal layer 10, the periodic structure may be formed on only one surface of the metal layer 10 on a side opposite to the substrate 15.

In this manner, the plurality of periodic structures can be formed on the surface of the metal layer 10 in the direction that the corrugated shape is formed repeatedly. Although the metal layer 10 according to this embodiment may have any one of the above-mentioned periodic structures, the explanation is made with respect to the metal layer 10 having the one-dimensional periodic structure where the x direction is the periodic direction.

Figure 3:
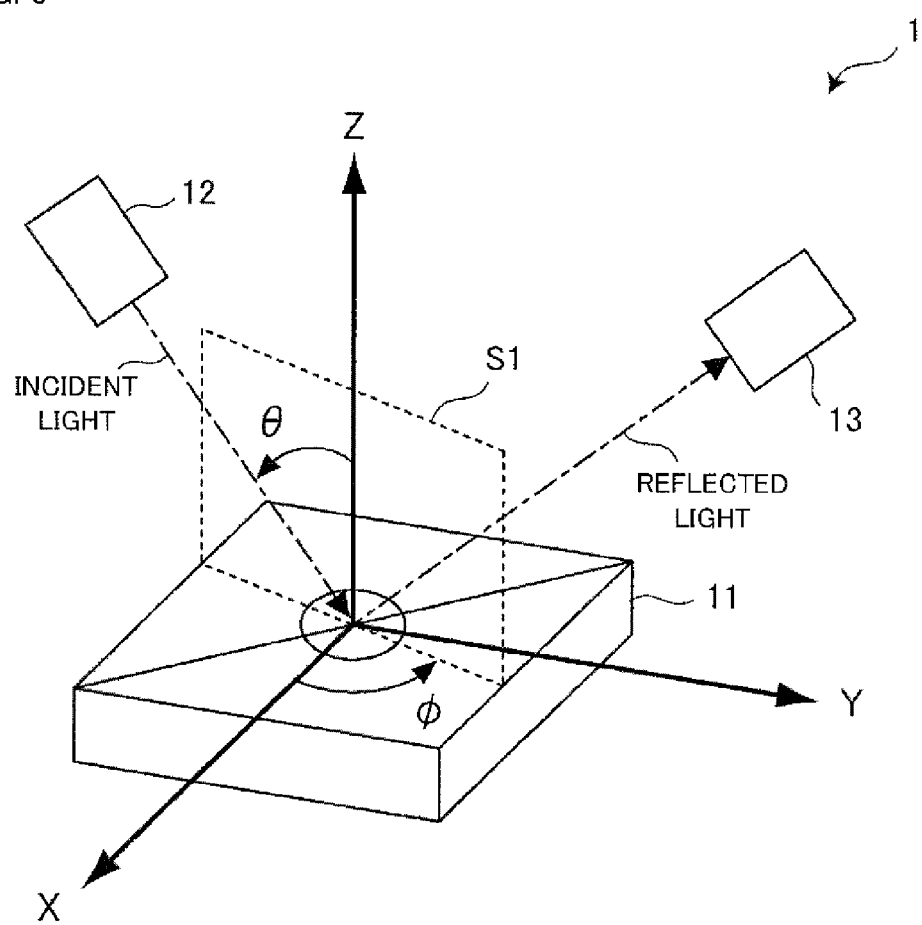
FIG. 3 is a schematic view of the surface plasmon sensor according to the first embodiment of the present invention.

As shown in FIG. 3, the reflection plate 11 is arranged obliquely such that the periodic direction (x direction) of the metal layer 10 and a surface S1 on which an incident light irradiated from the light source 12 is incident (hereinafter referred to as the plane of incidence S1, the detail of which being explained in detail later) do not intersect with each other orthogonally. The arrangement of the reflection plate 11 where the plane of incidence S1 and the periodic direction do not intersect with each other orthogonally is referred to as a conical mount. An angle made by the plane of incidence S1 and the periodic direction is referred to as an azimuth angle $\phi$. The reflection plate 11 according to this embodiment is arranged such that the angle azimuth angle $\phi$ satisfies $\phi \neq 0°$, 90°. The wavevector of the incident light and the 0-dimensional diffraction light (hereinafter referred to as reflected light) exist in the plane of incidence.

To explain this embodiment by returning to FIG. 1, on the reflection plate 11, a specimen 16 which constitutes a measuring object of a refractive index n, a reference substance which becomes the reference in the measurement of the refractive index n of the specimen 16 and the like are arranged.

The light source 12 is, for example, constituted of a light receiving element such as a semiconductor laser or a light emitting diode. An incident light of a p-wave is irradiated from the light source 12. The light source 12 irradiates the incident light while changing an angle θ at which the incident light is irradiated (hereinafter referred to as an angle of incidence θ, see FIG. 3). The light source 12 includes a drive device (not shown in the drawing) necessary for changing the incident angle θ. Also besides the drive device not shown in the drawing, an angle of incidence may be optically changed by using a laser diode array, for example.

The light receiving part 13 is constituted of a photo diode, for example. The light receiving part 13 receives a reflected light which contains a p-wave and an s-wave. The light receiving part 13 includes a drive device for receiving a reflected light in an interlocking manner with a change in an angle of incidence θ of an incident light. The light receiving part 13 may also optically change a reflection angle received by the light receiving part 13 using a photo diode array or the like.

The measurement part 14 measures the ellipticity of reflected light which the light receiving part 13 receives, and measures a change in the ellipticity. The measurement part 14 measures an angle of incidence $\theta_0$ at which the ellipticity becomes zero (hereinafter referred to as an absorption angle $\theta_0$) based on a change in measured ellipticity. The measurement part 14 measures a refractive index n of the specimen 16 based on the difference $\Delta\theta_0$ ($=\theta'_0-\theta_0$) between an absorption angle $\theta_0$ when the reference substance is arranged on the reflection plate 11 and an absorption angle $\theta'_0$ when the specimen 16 is arranged on the reflection plate 11.

Next, a method of measuring a refractive index n of the specimen 16 is explained.

Figure 4A:
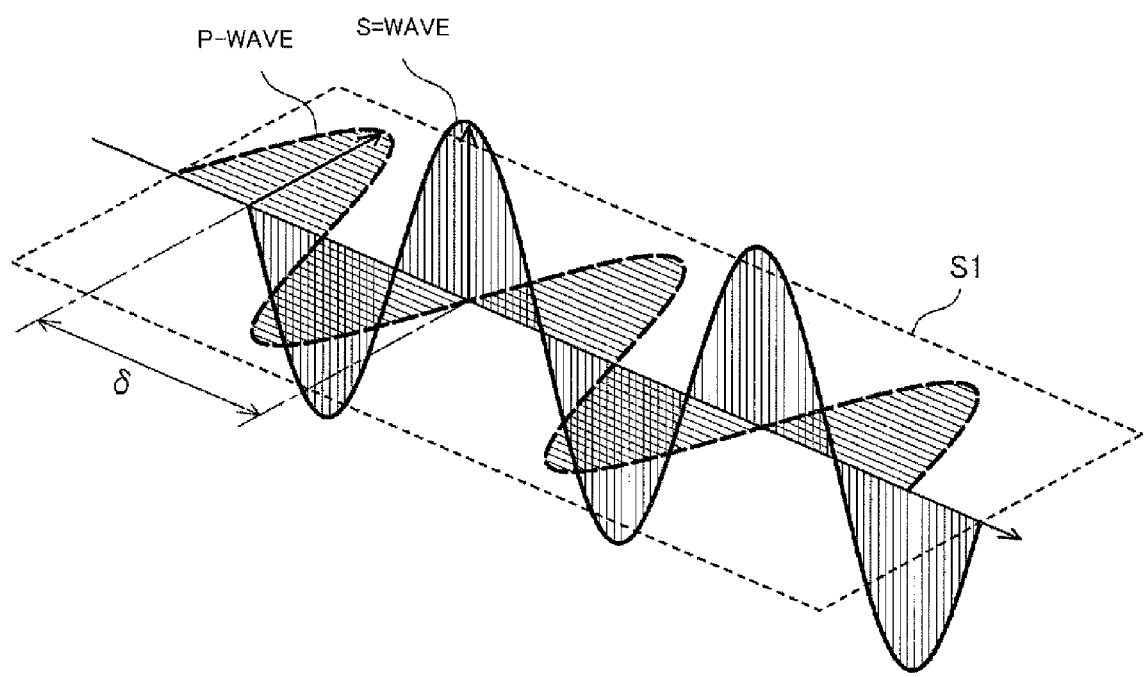
FIG. 4 is a view for explaining a reflected light according to the first embodiment of the present invention.
Figure 4B:
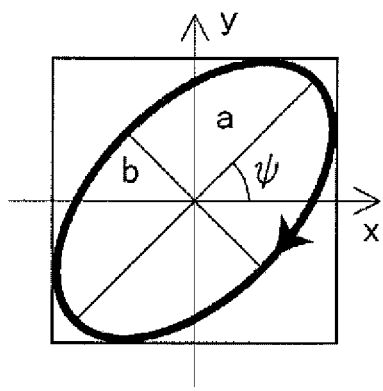

A reflected light which the light receiving part 13 receives is explained in conjunction with FIG. 4. As shown in FIG. 4(a), reflected light is divided into a p-wave component parallel to the plane of incidence S1 and an s-wave component perpendicular to the plane of incidence S1. To observe the light from the advancing direction of the light, it appears that an electric field vector of the light turns elliptically as shown in FIG. 4(b) corresponding to the phase difference δ between the p-wave and the s-wave. Here, assuming a length of the long axis as "a" and a length of the short axis as "b", the ellipticity tan χ is obtained by tan χ=b/a. An angle which the long axis of the ellipse which the electric field vector of the light makes with respect to the x direction is referred to as an inclination angle φ of the ellipse.

Figure 5:
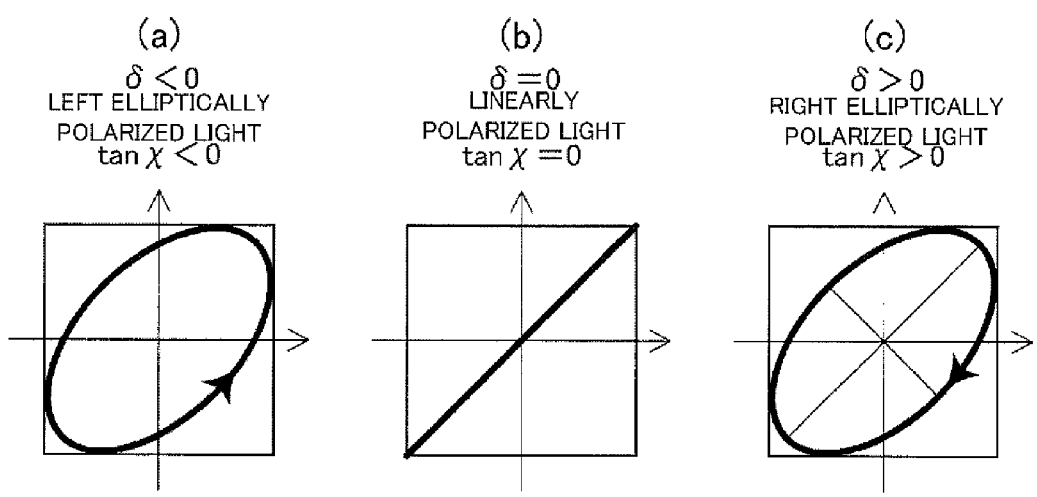
FIG. 5 is a view for explaining the reflected light according to the first embodiment of the present invention.

When the phase difference δ between the p-wave and the s-wave is smaller than zero, that is, the s-wave is retarded compared to the p-wave, as shown in FIG. 5(a), the light turns left elliptically as viewed in the advancing direction thereof. This light is called as a left elliptically polarized light. In this case, the ellipticity tan χ is smaller than zero.

When the phase difference δ between the p-wave and the s-wave is zero, that is, the phase of the p-wave and the phase of the s-wave are equal, as shown in FIG. 5(b), the light vibrates linearly as viewed in the advancing direction thereof. This light is called as a linearly polarized light. In this case, the ellipticity tan χ becomes zero.

When the phase difference δ between the p-wave and the s-wave is larger than zero, that is, the s-wave is advanced compared to the p-wave, as shown in FIG. 5(c), the light turns right elliptically as viewed in the advancing direction thereof. This light is called as a right elliptically polarized light. In this case, the ellipticity tan χ is larger than zero.

In this manner, the ellipticity tan χ of reflected light depends on the phase of the p-wave and the phase of the s-wave. Accordingly, it is possible to acquire the phase relationship between the p-wave and the s-wave by measuring the ellipticity tan χ of reflected light using the measurement part 14.

Figure 6:
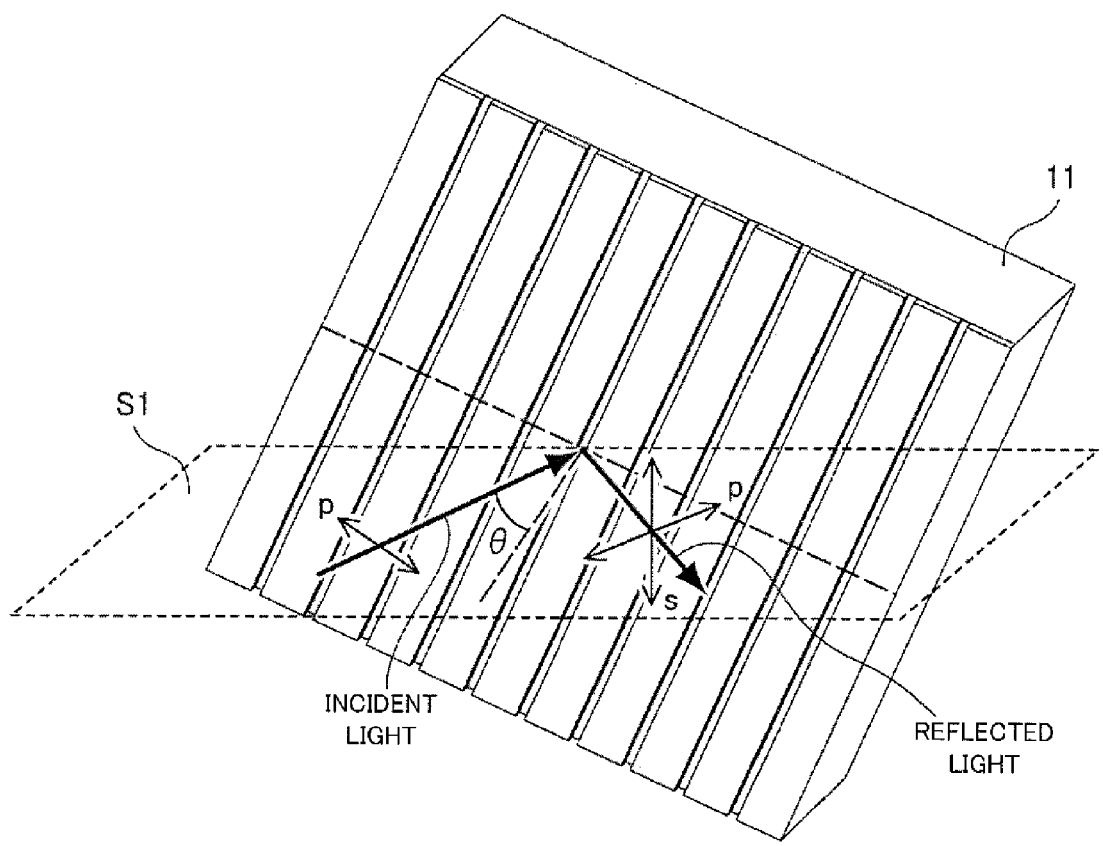
FIG. 6 is a view showing a reflection plate according to the first embodiment of the present invention.

In the case where the reflection plate 11 is arranged in a conical mount as shown in FIG. 6, when an incident light of a p-wave is incident on the reflection plate 11, a reflected light of a p-wave and an s-wave is obtained.

Next, a method of measuring a change in the ellipticity of reflected light when the specimen 16 is arranged on the reflection plate 11 (hereinafter referred to as ellipticity of the specimen 16) is explained in conjunction with FIG. 7. In this embodiment, a change in the ellipticity of the specimen 16 when an angle of incidence θ of the incident light is changed is measured.

The specimen 16 is arranged on the reflection plate 11 (S101), and an incident light having an angle of incidence θ and a wavelength λ is irradiated onto the specimen 16 from the light source 12 (S102). The light source 12 irradiates an incident light of a p-wave.

The light receiving part 13 receives light which is obtained by the reflection of the incident light on the reflection plate 11 through the specimen 16 (reflected light) (S103).

The measurement part 14 measures the ellipticity of reflected light from reflected light (S104).

The light source 12 changes an angle of incidence θ of the incident light which the light source 12 irradiates to θ+Δθ (S105).

When the ellipticity tan χ is not yet measured with respect to all incident angles θ within a range where the ellipticity is to be measured (no in step S106), the processing returns to step S102. On the other hand, when the ellipticity tan χ is measured with respect to all incident angles θ within the range where the ellipticity is to be measured (yes in step S106), ellipticity change measurement of the specimen 16 is finished.

Figure 7:
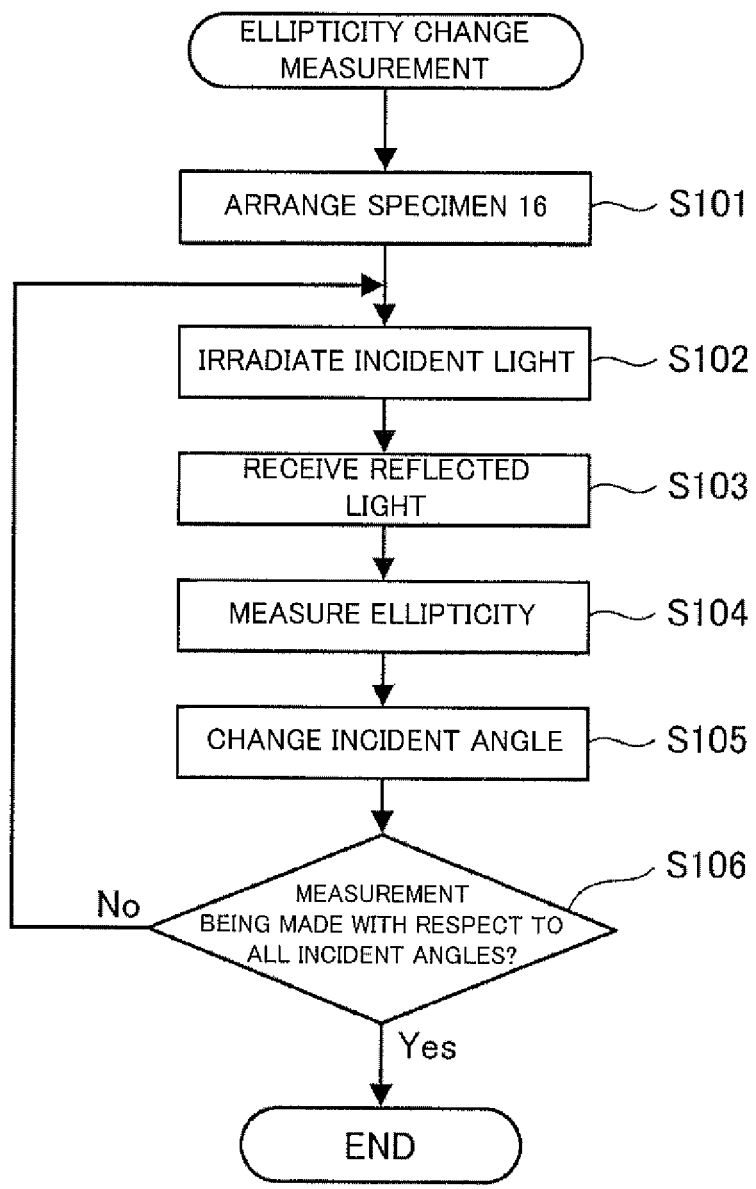
FIG. 7 is a view for explaining of a method of measuring a change in the ellipticity according to the first embodiment of the present invention.
Figure 8:
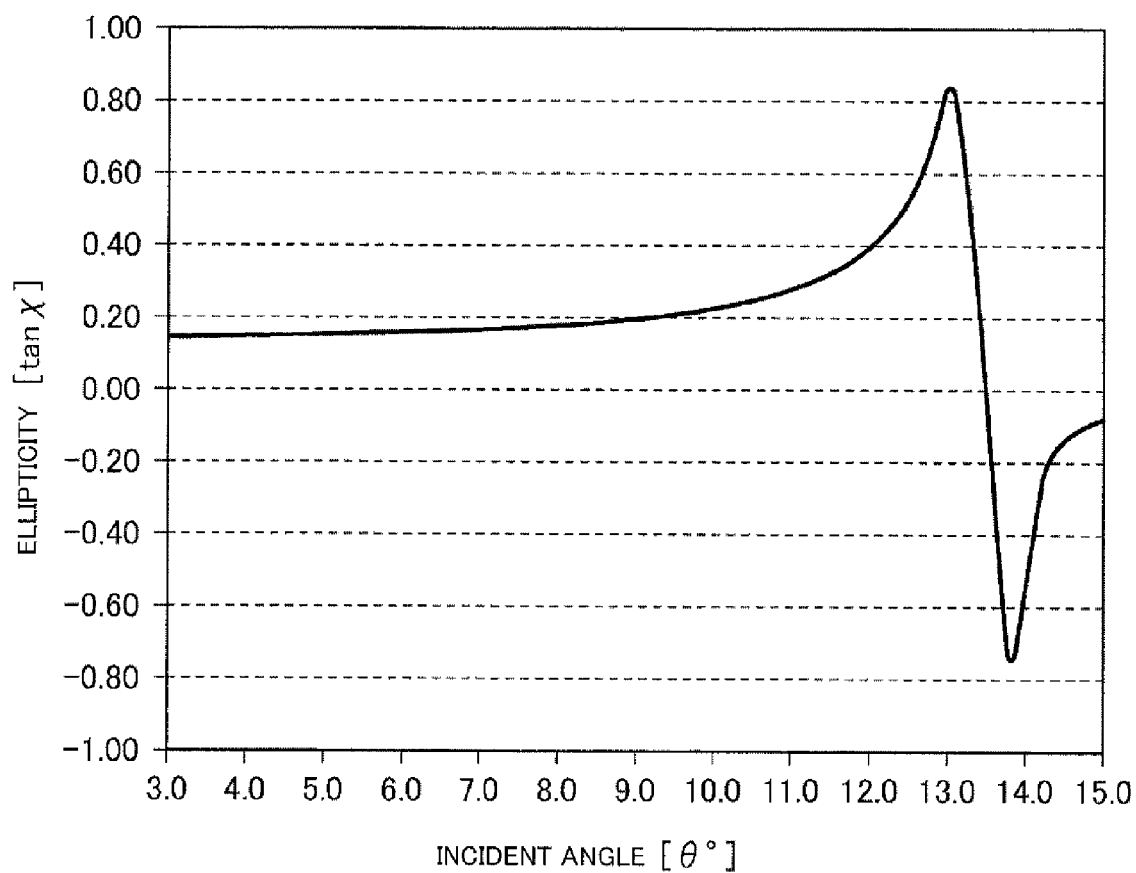
FIG. 8 is a graph showing of a change in the ellipticity of reflected light according to the first embodiment of the present invention.

FIG. 8 shows a simulation result of a change in the ellipticity tan χ with respect to respective incident angles θ which is measured by the measurement part 14. FIG. 8 is a graph showing a tan χ-θ characteristic curve of air constituting the specimen 16 which is measured in accordance with the flow-chart of the ellipticity change measurement shown in FIG. 7. Here, a holographic aluminum grating is used as the reflection plate 11. A depth H of grooves of the grating is set to 72 nm (H=72 nm), a period d of the grating is set to 556 nm (d=556 nm), an azimuth angle φ is set to 30° (φ=30°, a wavelength λ is set to 670 nm ($\lambda$=670 nm), and an angle of incidence $\theta$ is changed within a range of 3°<$\theta$<15°.

As shown in FIG. 8, the tan $\chi$-$\theta$ characteristic curve is changed to negative from positive before and after an absorption angle $\theta_0$ at which the ellipticity tan $\chi$ becomes zero.

Figure 9:
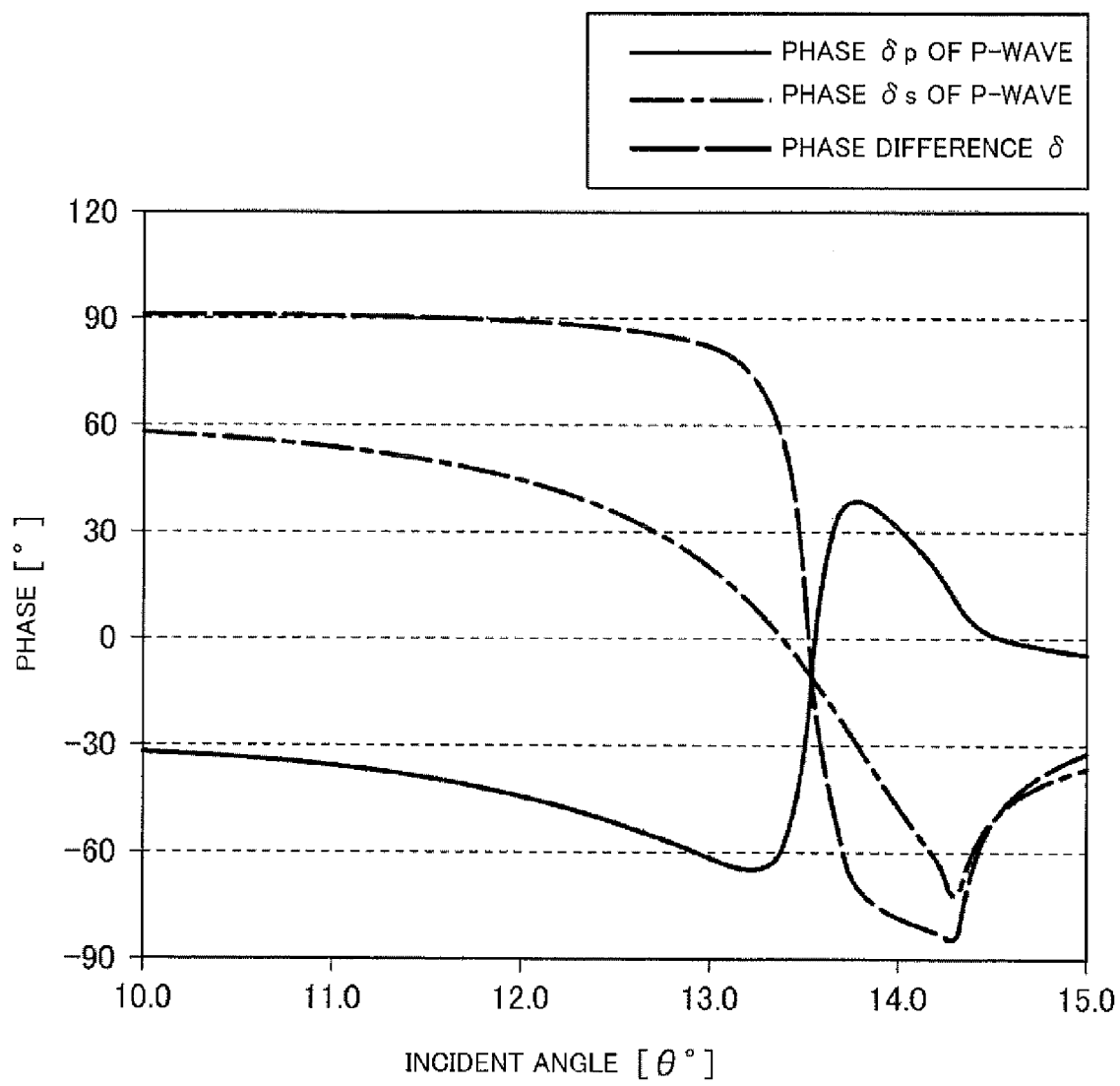
FIG. 9 is a graph showing of a phase of reflected light according to the first embodiment of the present invention.

Next, FIG. 9 shows a simulation result of a phase $\delta_p$, a phase $\delta_s$ and a phase difference $\delta$ at the respective incident angles $\theta$ measured by the measurement part 14. Here, air is used as the specimen 16, and the holographic aluminum grating is used as the reflection plate 11. A depth H of grooves of the grating is set to 72 nm (H=72 nm), a period d of the grating is set to 556 nm (d=556 nm), an azimuth angle $\phi$ is set to 30° ($\phi$=30°), a wavelength $\lambda$ is set to 670 nm ($\lambda$=670 nm), and an angle of incidence $\theta$ is changed within a range of 10°<$\theta$<15°.

A graph indicated by a solid line in FIG. 9 indicates a change in phase $\delta_p$ of a p-wave, and a graph indicated by a chained line in FIG. 9 indicates a change in phase $\delta_s$ of an s-wave. A graph indicated by a broken line indicates the phase difference $\delta$ (=$\delta_s$-$\delta_p$) between the p-wave and the s-wave.

The phase $\delta_p$ of the p-wave of reflected light sharply changes when the incident angle $\theta$ is within a range from 13° to 14°, while the phase $\delta_s$ of the s-wave changes smoothly. In FIG. 9, the incident angle $\theta$ at which the phase $\delta_p$ of the p-wave and the phase $\delta_s$ of the s-wave intersect with each other is the incident angle $\theta$ at which the phase difference $\delta$ between the p-wave and the s-wave becomes zero, and is an absorption angle $\theta_0$ at which the ellipticity tan $\chi$ becomes zero. The phase difference $\delta$ of reflected light changes from positive to negative or from negative to positive before and after the absorption angle $\theta_0$. That is, the ellipticity tan $\chi$ of reflected light changes from positive to negative or from negative to positive before and after the absorption angle $\theta_0$. Accordingly, the absorption angle $\theta_0$ at which the phase difference $\delta$ becomes zero can be measured by measuring tan $\chi$.

Figure 10:
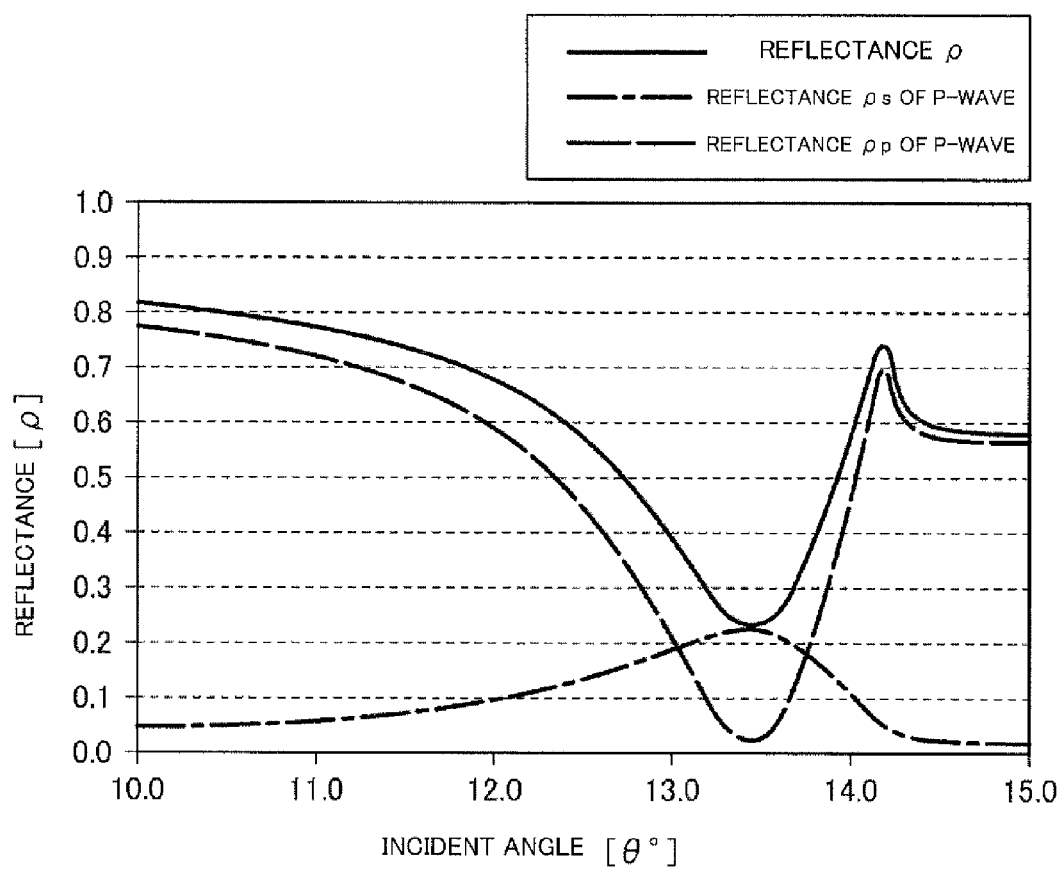
FIG. 10 is a graph showing of a reflectance of reflected light according to the first embodiment of the present invention.

FIG. 10 is a graph showing a simulation result of reflectance $\rho$ measured by the measurement part 14. In FIG. 10, a graph indicated by a broken line indicates the reflectance $\rho_p$ of a p-wave, and a graph indicated by a chained line indicates the reflectance $\rho_s$ of an s-wave. A graph indicated by a solid line indicates the reflectance $\rho$ of reflected light formed by adding the reflectances ($\rho_s$, $\rho_p$) of the p-wave and the s-wave.

As shown in FIG. 10, the incident angle at which the reflectance $\rho$ of reflected light becomes the smallest is the absorption angle $\theta_{sp}$. The surface plasmon sensor adopted in general which measures the refractive index n using the reflectance $\rho$ of reflected light measures a change in the reflectance $\rho$ of a p-wave while changing an angle of incidence, and measures the absorption angle $\theta_{sp}$ by performing the smallest point detection. On the other hand, the surface plasmon sensor 1 according to this embodiment does not measure a change in reflectance $\rho$ but measures a change in the ellipticity tan $\chi$, and measures the absorption angle $\theta_0$ by performing the detection of a zero point at which the ellipticity tan $\chi$ becomes zero. Although the absorption angle $\theta_0$ of the ellipticity tan $\chi$ and the absorption angle $\theta_{sp}$ of the reflectance $\rho$ do not necessarily take the same value, they take values extremely close to each other and hence, the surface plasmon sensor 1 according to this embodiment measures the refractive index n of the specimen 16 using the absorption angle $\theta_0$ of a light having the ellipticity tan $\chi$ in place of using the absorption angle $\theta_{sp}$ of the reflectance $\rho$.

Figure 11:
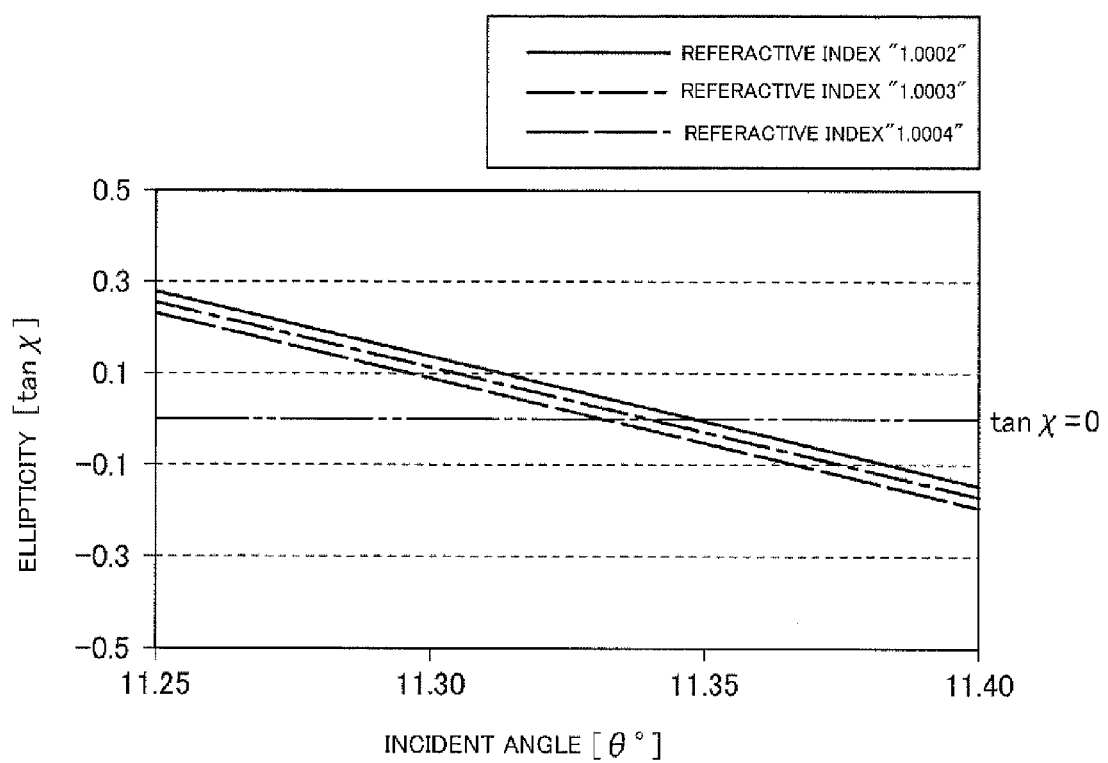
FIG. 11 is a graph showing an incident angle characteristic of a light having the ellipticity according to the first embodiment of the present invention.
Figure 12:
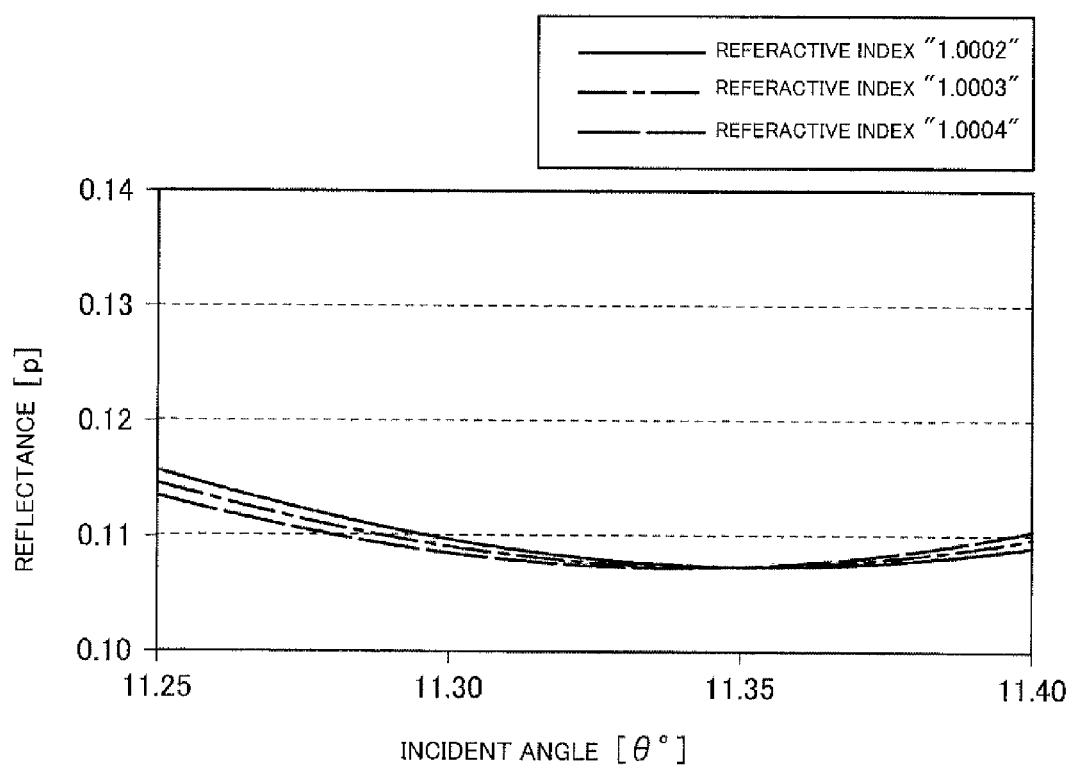
FIG. 12 is a graph showing an incident angle characteristic of a light having reflectance according to the first embodiment of the present invention.

Next, using FIG. 11 and FIG. 12, the explanation is made with respect to a point that the surface plasmon sensor 1 according to this embodiment can measure a refractive index n with high accuracy. With respect to specimens 16 having the refractive indices n of "1.0002", "1.0003" and "1.0004" respectively, incident angle characteristics of reflected light having the ellipticity tan $\chi$ are shown in FIG. 11, and incident angle characteristics of reflected light having the reflectance $\rho$ are shown in FIG. 12. Both FIG. 11 and FIG. 12 are graphs which show a simulation result. Both FIG. 11 and FIG. 12 indicate incident angle characteristics in the vicinity of the absorption angle $\theta_0$, $\theta_{sp}$ in an enlarged manner. In FIG. 11 and FIG. 12, a solid line indicates the incident angle characteristic at the refractive index "1.0002", a chained line indicates the incident angle characteristic at the refractive index "1.0003", and a broken line indicates the incident angle characteristic at the refractive index "1.0004".

In FIG. 11, incident angle characteristics of lights having the respective refractive indices n are formed into approximately linear shapes. The absorption angle $\theta_0$ of a light having the ellipticity tan $\chi$ is an angle of incidence at which the ellipticity tan $\chi$ becomes zero and hence, the absorption angle $\theta_0$ of a light having the ellipticity tan $\chi$ can be measured by performing the zero point detection of the respective incident angle characteristics. The zero point can be detected easily with high accuracy. With respect to the absorption angles $\theta_0$ at the respective refractive indices n shown in FIG. 11, the absorption angle $\theta_0$ is 11.349° (absorption angle $\theta_0$=11.349° at the refractive index "1.0002", the absorption angle $\theta_0$ is 11.342° (absorption angle $\theta_0$=11.342°) at the refractive index "1.0003", and the absorption angle $\theta_0$ is 11.334° (absorption angle $\theta_0$=11.334°) at the refractive index "1.0004".

On the other hand, in FIG. 12, incident angle characteristics of lights having the respective refractive indices n are formed into non-linear shapes drawing a downwardly projecting gentle curve. The absorption angle $\theta_{sp}$ of the reflectance $\rho$ is an angle of incidence at which the reflectance $\rho$ becomes the smallest and hence, the absorption angle $\theta_{sp}$ of the reflectance $\rho$ can be measured by performing the smallest point detection of the respective incident angle characteristics. However, when the difference between the respective refractive indices n is small and a Q value of the incident angle characteristic is small, the smallest points appear to overlap with each other as shown in FIG. 12 and hence, it is difficult to measure the absorption angle $\theta_{sp}$ with high accuracy.

As describe above, the incident angle characteristic of the ellipticity tan $\chi$ becomes approximately linear in the vicinity of the absorption angle $\theta_0$ and hence, even when the difference in the refractive index n is small, the difference can be detected as the difference in absorption angle $\theta_0$.

Accordingly, in the surface plasmon sensor 1 according to this embodiment, firstly, the reference substance whose refractive index $n_s$ is already known is arranged on the reflection plate 11 as the specimen 16, and a change in the ellipticity tan $\chi$ of reflected light is measured in accordance with steps shown in FIG. 7, and the absorption angle $\theta_0$ is measured.

Next, the specimen 16 whose refractive index n is to be measured is arranged on the reflection plate 11, and the absorption angle $\theta'_0$ at which the ellipticity tan $\chi$ becomes zero is measured in accordance with steps substantially equal to the steps for measuring the absorption angle $\theta_0$ with respect to the reference substance.

The difference $\Delta n$(=n-$n_s$) between the refractive index $n_s$ of the reference substance and the refractive index n of the specimen 16 is measured based on the difference $\Delta\theta_0$ (=$\theta'_0$-$\theta_0$) between the measured absorption angles.

The absorption angle $\theta_0$ of the reference substance is measured in the above-mentioned a measuring method. However, when the refractive index $n_s$ and the absorption angle $\theta_0$ of the reference substance are already known, the measurement may be omitted.

The measurement part 14 may acquire the incident angle θ from the light source 12 each time the ellipticity tan χ of reflected light is measured or may acquire the incident angle θ from the light source 12 when the ellipticity tan χ becomes zero. Alternatively, the measurement part 14 may acquire the incident angle when the ellipticity tan χ is measured based on a range of the incident angle θ and an amount of change in the incident angle (Δθ in step S105). In this manner, the measurement part 14 may perform the above-mentioned method of measuring the refractive index n by controlling the light source 12, or a control part not shown in the drawing is provided and the respective parts may be controlled by the control part.

As described above, the surface plasmon sensor according to this embodiment measures the refractive index n of the specimen 16 based on a change in the ellipticity tan χ, to be more specific, based on the absorption angle $\theta_0$ at which the ellipticity tan χ becomes zero. The incident angle characteristic of the ellipticity tan χ becomes approximately linear in the vicinity of the absorption angle $\theta_0$ and hence, the absorption angle $\theta_0$ at which the ellipticity tan χ becomes zero can be measured by performing the zero point detection whereby the complicated detection such as the smallest point detection becomes unnecessary thus enabling the easy measurement of the absorption angle $\theta_0$ with high accuracy. Accordingly, the refractive index n of a substance such as a gas which exhibits minute difference in refractive index n, for example, can be also measured.

Second Embodiment

Figure 13:
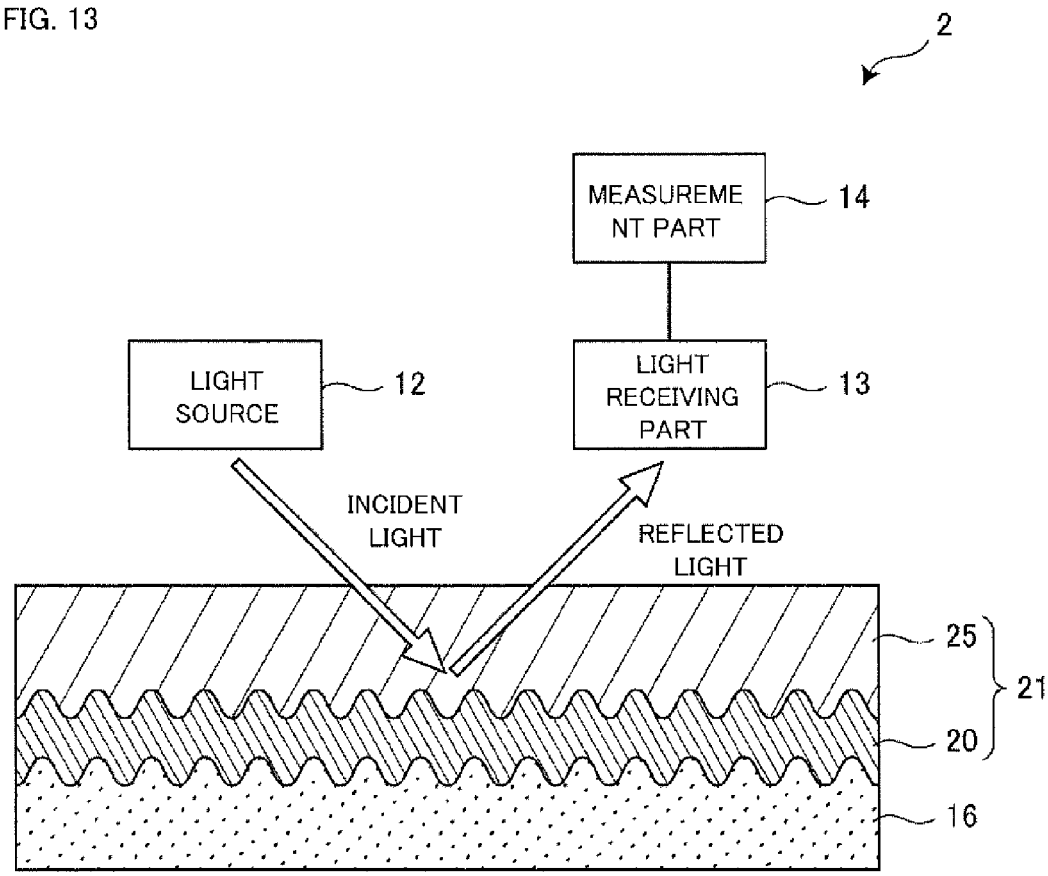
FIG. 13 is a schematic view of a surface plasmon sensor according to a second embodiment of the present invention.

A surface plasmon sensor 2 according to the second embodiment of the present invention is explained. FIG. 13 is a view showing the schematic constitution of the surface plasmon sensor 2. The surface plasmon sensor 2 according to this embodiment differs from the surface plasmon sensor 1 shown in FIG. 1 with respect to a point that a metal layer 20 of a reflection plate 21 has a one-dimensional thin film periodic structure shown in FIG. 2(c) and a point that an incident light is incident from a substrate 25 side.

The reflection plate 21 includes: a substrate 25 which allows light to pass therethrough as in the case of a silicon substrate; and the metal layer 20 which includes the one-dimensional thin film periodic structure. The reflection plate 21 is formed by laminating the substrate 25 and the metal layer 20 sequentially from a side close to the light source 12. The specimen 16 is arranged on a surface of the metal layer 20 on a side opposite to the substrate 25.

The surface plasmon sensor 2 according to the second embodiment is substantially equal the surface plasmon sensor 1 according to the first embodiment with respect to the constitutions other than the above-mentioned constitution and a method of measuring a refractive index. Accordingly, the explanation of the constitutions other than the above-mentioned constitution and the method of measuring the refractive index is omitted. Although the periodic structure is formed on both surfaces of the metal layer 20 in this embodiment, the periodic structure may be formed on only one surface of the metal layer 20 on which the specimen 16 is arranged.

As described above, the surface plasmon sensor 2 according to this embodiment can measure a refractive index n of the specimen 16 in the same manner as the first embodiment even when the specimen 16 cannot be arranged between the light source 12 and the reflection plate 21.

Third Embodiment

Figure 14:
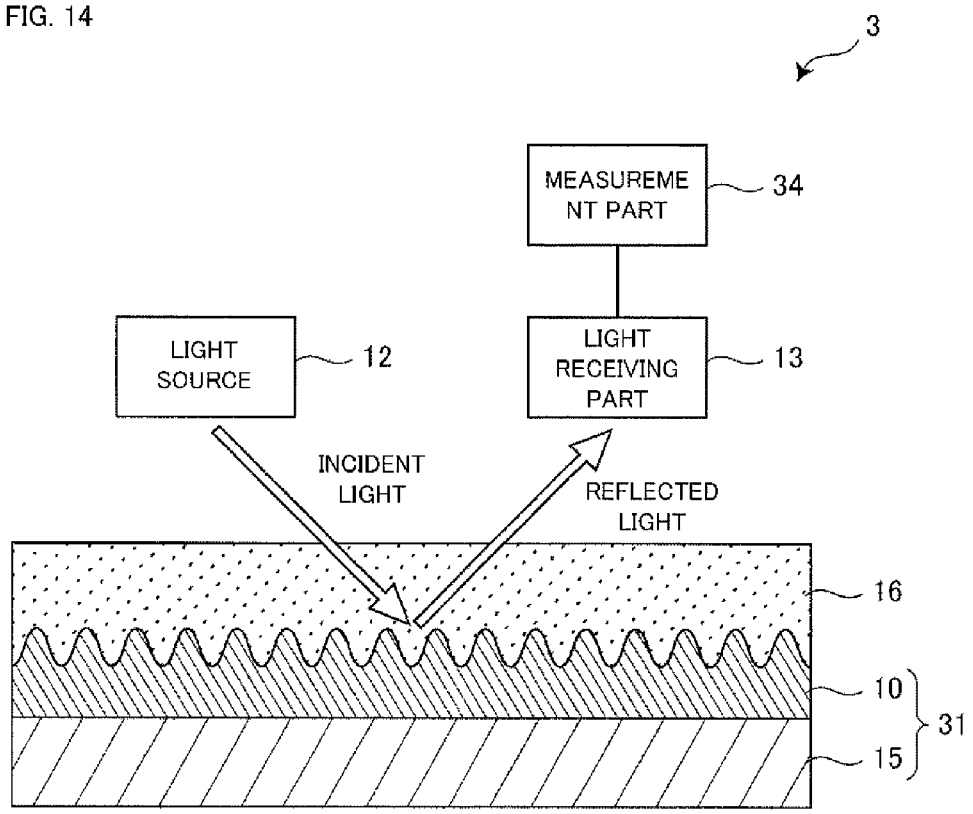
FIG. 14 is a schematic view of a surface plasmon sensor according to a third embodiment of the present invention.

A surface plasmon sensor 3 according to the third embodiment of the present invention is explained. FIG. 14 is a view showing the schematic constitution of the surface plasmon sensor 3. The surface plasmon sensor 3 according to this embodiment differs from the surface plasmon sensor 1 shown in FIG. 1 with respect to a point that an angle of incidence θ and a wavelength are set to constant values, and a change in the ellipticity tan χ is measured while changing an azimuth angle φ of a reflection plate 31.

The reflection plate 31 has a drive device not shown in the drawing, and rotates such that an azimuth angle φ changes.

A measurement part 34 measures a change in the ellipticity of a reflected light which a light receiving part 13 receives.

The measurement part 34 measures an azimuth angle $\phi_0$ at which the measured ellipticity becomes zero (hereinafter referred to as an absorption azimuth angle $\phi_0$. The measurement part 34 measures the difference Δn in refractive index between a specimen 16 and a reference substance based on the difference $\Delta\phi_0 (=\phi'_0 - \phi_0)$ between an absorption azimuth angle $\phi_0$ where the reference substance is arranged on the reflection plate 11 and an absorption azimuth angle $\phi'_0$ where the specimen 16 is arranged on the reflection plate 11.

The surface plasmon sensor 3 is substantially equal the surface plasmon sensor 1 shown in FIG. 1 with respect to the constitutions other than the above-mentioned constitution and hence, the explanation of the constitutions other than the above-mentioned constitution is omitted.

Figure 15:
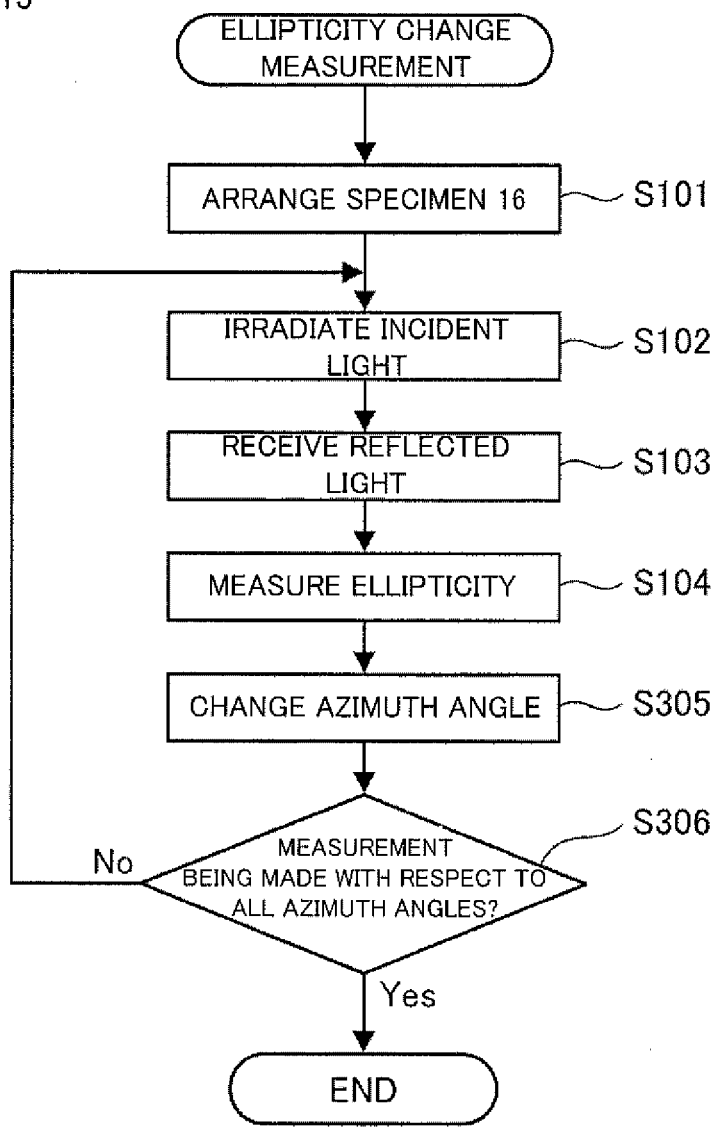
FIG. 15 is a view for explaining a method of measuring a change in the ellipticity according to a third embodiment of the present invention.

A method of measuring a change in the ellipticity tan χ of a reflected light when an azimuth angle φ of the reflection plate 31 is changed is explained in conjunction with FIG. 15. The processing up to step S104 is substantially equal the corresponding processing shown in FIG. 7 and hence, the explanation of the processing is omitted.

When the ellipticity tan χ of reflected light is measured, the reflection plate 31 changes an azimuth angle φ thereof to φ+Δφ (S305). When the ellipticity tan χ is not yet measured with respect to all azimuth angles φ at which a change in the ellipticity is to be measured (no in S306), the processing returns to step S102. On the other hand, when the ellipticity tan χ is measured with respect to all azimuth angles φ (yes in S306), the measurement of the specimen 16 is finished.

Figure 16:
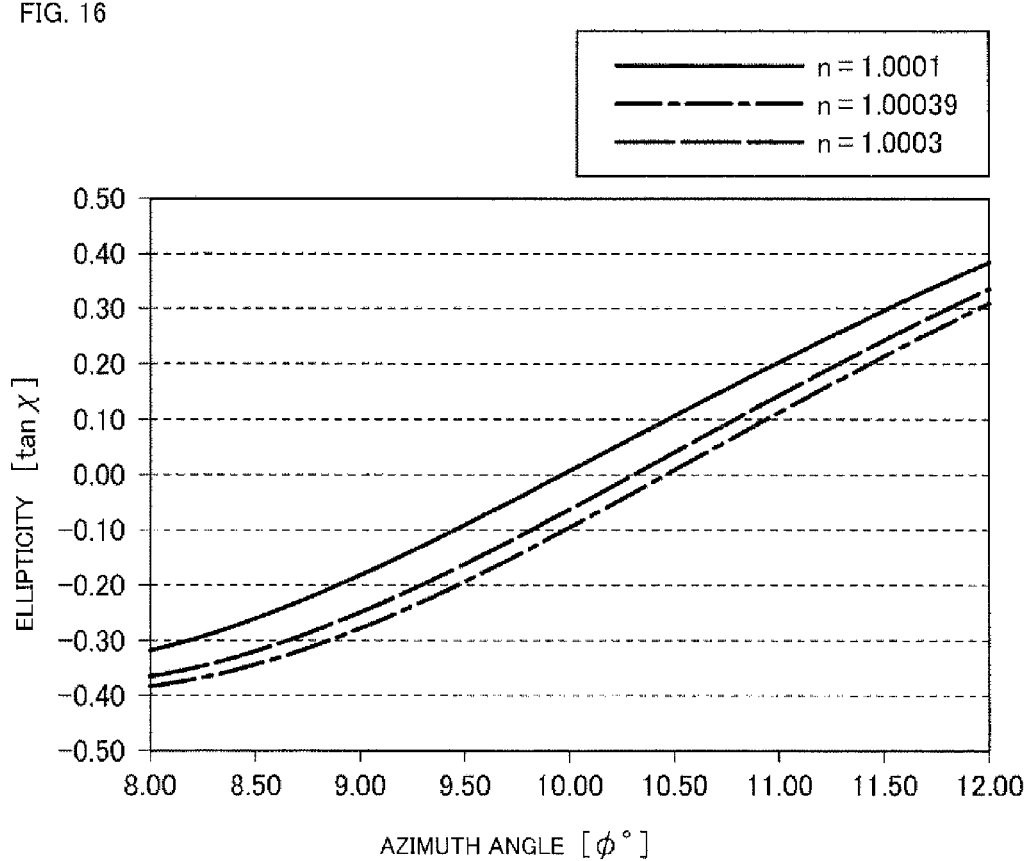
FIG. 16 is a graph showing an azimuth angle characteristic of the ellipticity according to the third embodiment of the present invention.

The explanation is made with respect to a point that the surface plasmon sensor 3 according to this embodiment can measure a refractive index n in conjunction with FIG. 16. With respect to specimens 16 having the refractive indices n of "1.0003", "1.00039" and "1.0001" respectively, azimuth angle characteristics of reflected lights having the ellipticity tan χ are shown in FIG. 16. A solid line indicates the azimuth angle characteristic at the refractive index "1.0001", a broken line indicates the azimuth angle characteristic at the refractive index "1.0003", and a chained line indicates the azimuth angle characteristic at the refractive index "1.00039". FIG. 16 shows a simulation result when a change in the ellipticity tan χ with respect to air is measured under conditions where an angle of incidence θ is set to 11.3° (θ=11.3°) and a wavelength λ is set at 670 nm (λ=670 nm).

In FIG. 16, the azimuth angle characteristics of lights having respective refractive indices n are approximately linear. Accordingly, the absorption azimuth angle $\phi_0$ at which the ellipticity tan χ becomes zero can be measured easily and with high accuracy also by using the azimuth angle characteristics in the same manner as the incident angle characteristics according to the first embodiment.

In the surface plasmon sensor 1 according to this embodiment, firstly, the reference substance whose refractive index $n_s$ is already known is arranged on the reflection plate 31, and a change in the ellipticity tan χ when an azimuth angle is changed is measured in accordance with steps shown in FIG.

15, and the absorption azimuth angle $\phi_0$ at which the ellipticity tan $\chi$ become zero is measured.

Next, the specimen 16 whose refractive index n is to be measured is arranged on the reflection plate 31, and the absorption azimuth angle $\phi'_0$ at which the ellipticity tan $\chi$ becomes zero is measured in accordance with steps substantially equal to the steps for measuring the absorption azimuth angle $\phi_0$ with respect to the reference substance.

The difference $\Delta n(=n-n_s)$ between the refractive index $n_s$ of the reference substance and the refractive index n of the specimen 16 is measured based on the difference $\Delta\phi_0$ ($=\phi'_0-\phi_0$) between the measured absorption azimuth angles.

The absorption azimuth angle $\phi_0$ of the reference substance is measured in the above-mentioned a measuring method. However, when the refractive index $n_s$ and the absorption azimuth angle $\phi_0$ of the reference substance are already known, the measurement may be omitted.

The measurement part 34 may acquire the azimuth angle $\phi$ of the reflection plate 31 from the reflection plate 31 each time the ellipticity tan $\chi$ of reflected light is measured or may acquire the azimuth angle $\phi$ from the reflection plate 31 when the ellipticity tan $\chi$ becomes zero. Alternatively, the measurement part 34 may acquire the azimuth angle $\phi$ when the ellipticity tan $\chi$ is measured based on a range of the azimuth angle $\phi$ and an amount of change in the azimuth angle $\phi$ ($\Delta\phi$ in step S305). In this manner, the measurement part 34 may perform the above-mentioned method of measuring the refractive index n by controlling the reflection plate 31 or a control part not shown in the drawing is provided and the respective parts may be controlled by the control part.

As described above, according to the surface plasmon sensor 3 of this embodiment, the ellipticity changes by changing the azimuth angle $\phi$ even when the incident angle $\theta$ is set at a constant value and hence, the refractive index n of the specimen 16 can be measured easily and with high accuracy without changing the incident angle $\theta$.

Fourth Embodiment

Figure 17:
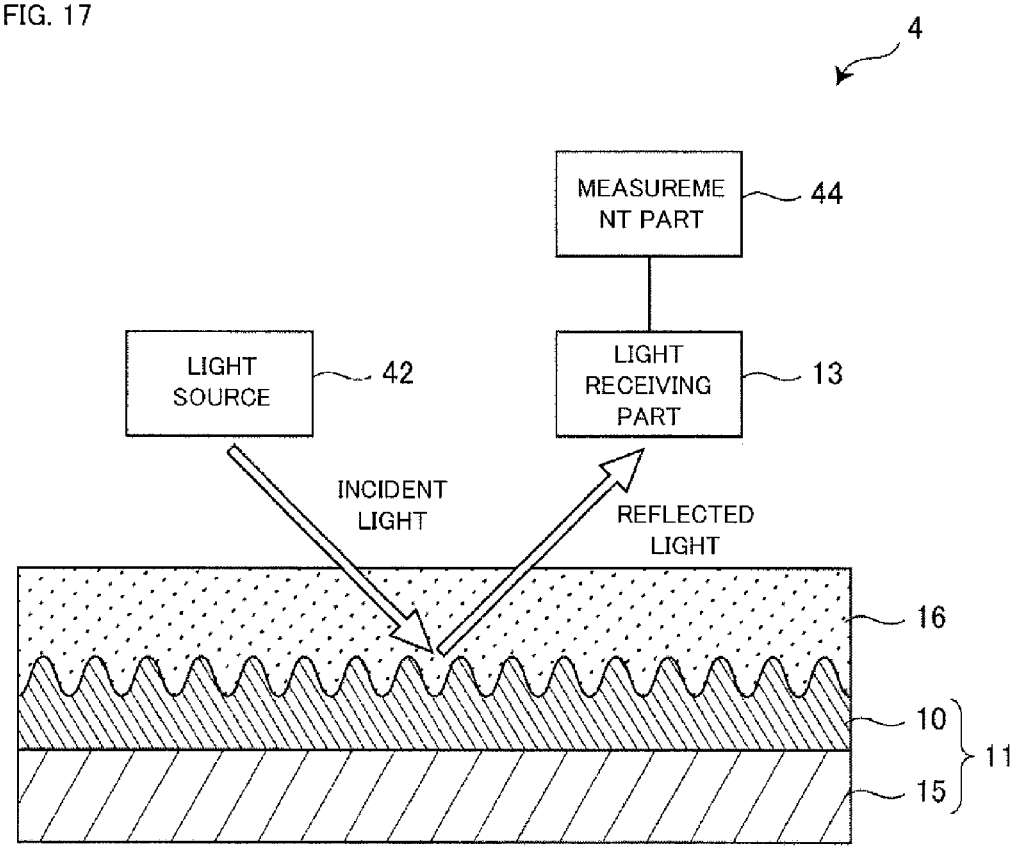
FIG. 17 is a schematic view of a surface plasmon sensor according to a fourth embodiment of the present invention.

A surface plasmon sensor 4 according to the fourth embodiment of the present invention is explained. FIG. 17 is a view showing the schematic constitution of the surface plasmon sensor 4. The surface plasmon sensor 4 according to this embodiment differs from the surface plasmon sensor 1 shown in FIG. 1 with respect to a point that an angle of incidence $\theta$ and an azimuth angle $\phi$ are set at constant values, and a change in the ellipticity tan $\chi$ is measured while changing a wavelength $\lambda$ of an incident light.

A light source 42 is constituted of a semiconductor laser, for example. The semiconductor laser can change a wavelength of an incident light in response to a control signal inputted to the light source 42 from a control part. The light source 42 may be configured to include the control part. The light source 42 irradiates an incident light while changing a wavelength $\lambda$ of the incident light.

A measurement part 44 measures a change in the ellipticity of a reflected light which a light receiving part 13 receives. The measurement part 44 measures a wavelength $\lambda_0$ at which the measured ellipticity becomes zero (hereinafter referred to as absorption wavelength $\lambda_0$). The measurement part 44 measures the difference $\Delta n$ in refractive index between a specimen 16 and a reference substance based on the difference $\Delta\lambda_0$ ($=\lambda'_0-\lambda_0$) between an absorption wavelength $\lambda_0$ where the reference substance is arranged on the reflection plate 11 and an absorption wavelength $\lambda'_0$ where the specimen 16 is arranged on the reflection plate 11.

The surface plasmon sensor 4 is substantially equal the surface plasmon sensor 1 shown in FIG. 1 with respect to the constitutions other than the above-mentioned constitution and hence, the explanation of the constitutions other than the above-mentioned constitution is omitted.

Figure 18:
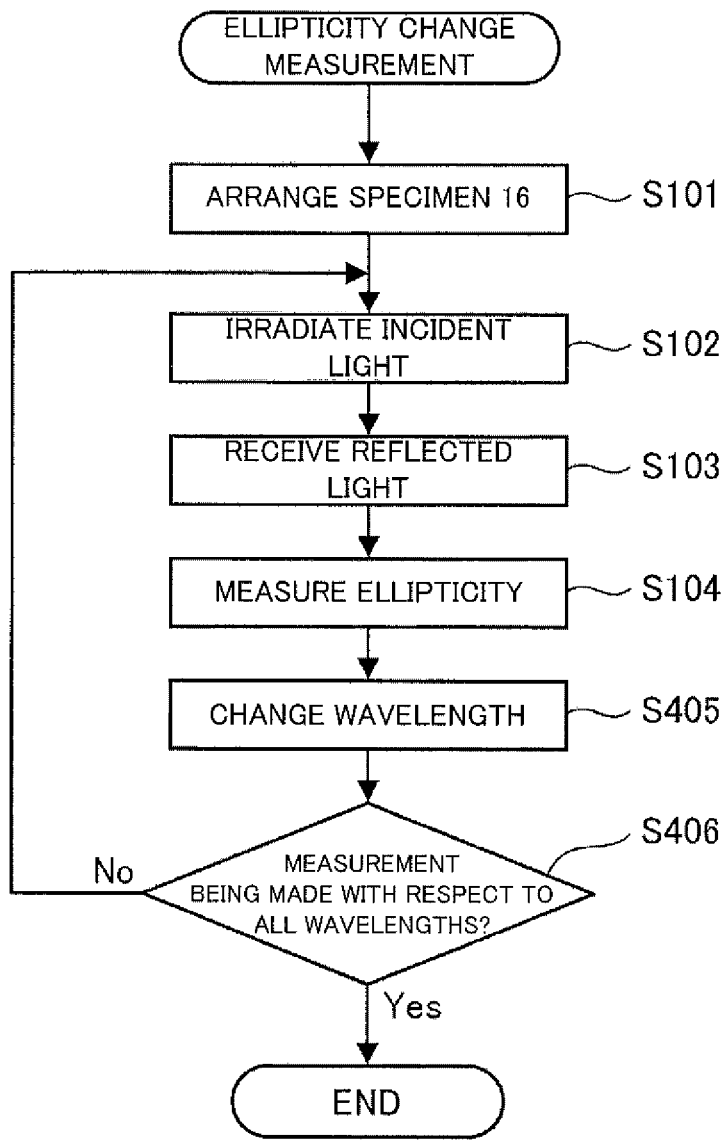
FIG. 18 is a view for explaining a method of measuring a change in the ellipticity according to the fourth embodiment of the present invention.

A method of measuring a change in the ellipticity tan $\chi$ of a reflected light when a wavelength $\lambda$ of an incident light is changed is explained in conjunction with FIG. 18. The processing up to step S104 is equal to the corresponding processing shown in FIG. 7 and hence, the explanation of the processing is omitted.

After the ellipticity tan $\chi$ of reflected light is measured, the light source 42 changes a wavelength $\lambda$ of light which the light source 42 irradiates to $\lambda+\Delta\lambda$ (S405). When the ellipticity tan $\chi$ is not yet measured with respect to all wavelengths within a range where a change in the ellipticity is to be measured (no in S406), the processing returns to step S102. On the other hand, when the ellipticity tan $\chi$ is measured with respect to all wavelengths (yes in S406), the measurement of the specimen 16 is finished.

Figure 19:
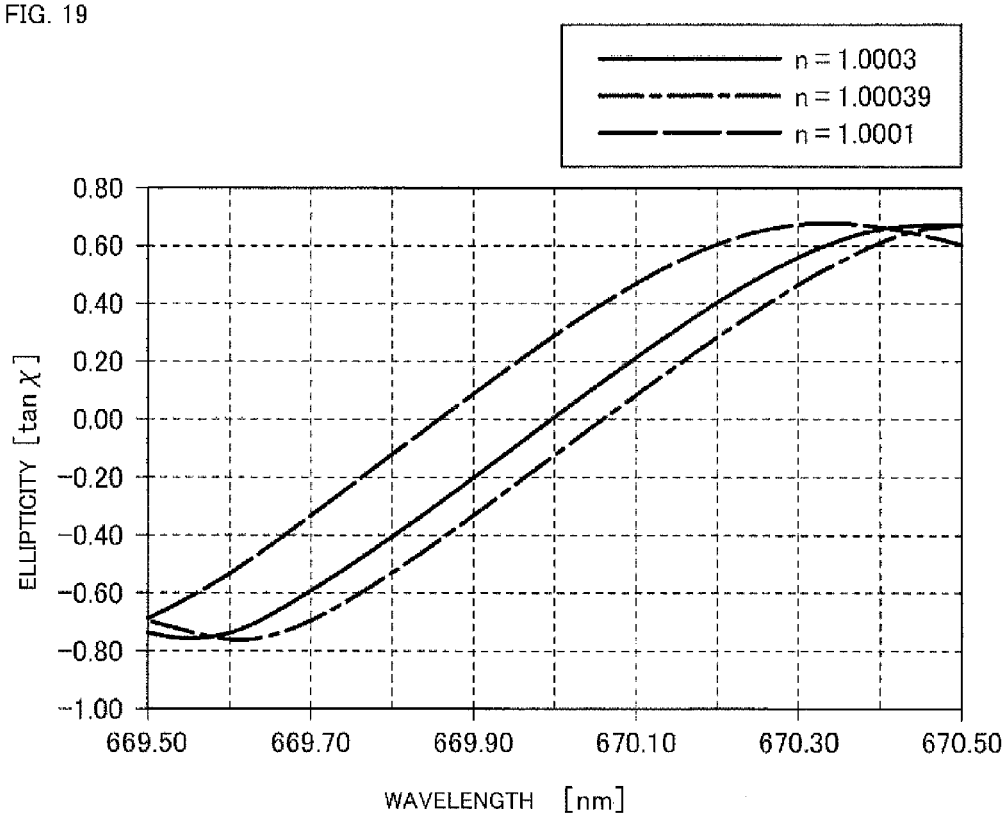
FIG. 19 is a graph showing a wavelength characteristic of the ellipticity according to the fourth embodiment of the present invention.

The explanation is made with respect to a point that the surface plasmon sensor 4 according to this embodiment can measure a refractive index n in conjunction with FIG. 19. With respect to specimens 16 having the refractive indices n of "1.0003", "1.00039" and "1.0001" respectively, wavelength characteristics of reflected lights having the ellipticity tan $\chi$ are shown in FIG. 19. A broken line indicates the wavelength characteristic at the refractive index "1.0001", a solid line indicates the wavelength characteristic at the refractive index "1.0003", and a chained line indicates the wavelength characteristic at the refractive index "1.00039". FIG. 19 shows a simulation result when a change in the ellipticity tan $\chi$ with respect to air is measured under conditions where an angle of incidence is set to 11.193° ($\theta=11.193°$) and an azimuth angle $\phi$ is set at 5° ($\phi=5°$).

In FIG. 19, the wavelength characteristics of lights having respective refractive indices n are approximately linear. Accordingly, the absorption wavelength $\lambda_0$ at which the ellipticity tan $\chi$ becomes zero can be measured easily and with high accuracy also by using the wavelength characteristics in the same manner as the incident angle characteristics according to the first embodiment.

In the surface plasmon sensor 4 according to this embodiment, firstly, the reference substance whose refractive index $n_s$ is already known is arranged on the reflection plate 11, and a change in the ellipticity tan $\chi$ when a wavelength is changed is measured in accordance with steps shown in FIG. 18, and the absorption wavelength $\lambda_0$ at which the ellipticity tan $\chi$ becomes zero is measured.

Next, the specimen 16 whose refractive index n is to be measured is arranged on the reflection plate 11, and the absorption wavelength $\lambda'_0$ at which the ellipticity tan $\chi$ becomes zero is measured in accordance with steps substantially equal to the steps for measuring the absorption wavelength $\lambda_0$ of the reference substance.

The difference $\Delta n(=n-n_s)$ between the refractive index $n_s$ of the reference substance and the refractive index n of the specimen 16 is measured based on the difference $\Delta\lambda_0$ ($=\lambda'_0-\lambda_0$) between the measured absorption wavelengths.

The absorption wavelength $\lambda_0$ of the reference substance is measured in the above-mentioned measuring method. However, when the refractive index $n_s$ and the absorption wavelength $\lambda_0$ of the reference substance are already known, the measurement may be omitted.

The measurement part 44 may acquire a wavelength $\lambda$ of an incident light from the light source 42 each time the ellipticity tan $\chi$ of reflected light is measured or may acquire the wavelength λ when the ellipticity tan χ becomes zero from the light source 42. Alternatively, the measurement part 44 may acquire the wavelength λ when the ellipticity tan χ is measured based on a range of the wavelength λ and an amount of change in the wavelength λ (Δλ in step S405). In this manner, the measurement part 44 may perform the above-mentioned method of measuring the refractive index n by controlling the light source 42 or a control part not shown in the drawing is provided and the respective parts may be controlled by the control part.

As described above, according to the surface plasmon sensor 4 of this embodiment, the ellipticity changes by changing the wavelength λ even when the incident angle θ is set at a constant value and hence, the refractive index n of the specimen 16 can be measured easily and with high accuracy without changing the incident angle θ. Since it is unnecessary to change the incident angle θ, the light source 42 does not require a drive source whereby the surface plasmon sensor 4 can be miniaturized.

Fifth Embodiment

Figure 20:
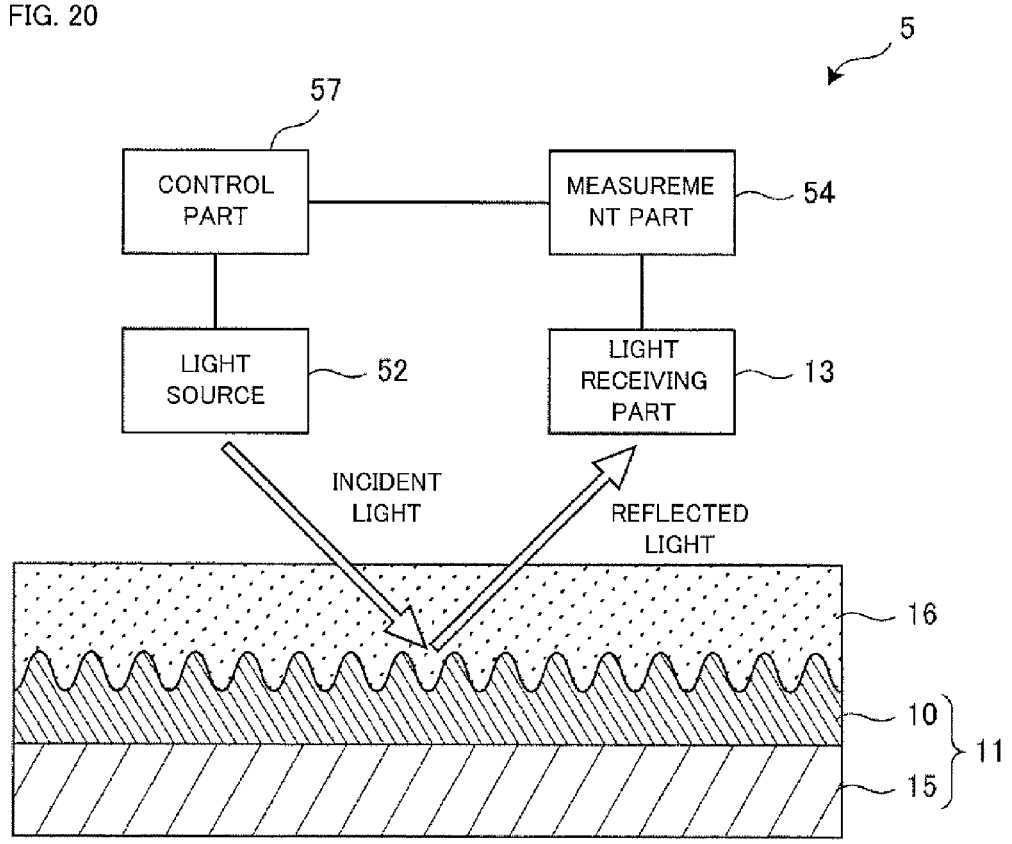
FIG. 20 is a schematic view of a surface plasmon sensor according to a fifth embodiment of the present invention.

A surface plasmon sensor 5 according to the fifth embodiment of the present invention is explained in conjunction with FIG. 20. The surface plasmon sensor 5 according to the this embodiment includes a control part 57 which controls a wavelength λ of an incident light which a light source 52 irradiates based on the ellipticity tan χ which a measurement part 54 measures.

The light source 52 controls a semiconductor laser (not shown in the drawing) based on a control signal inputted to the light source 52 from the control part 57, and irradiates an incident light having a wavelength λ. The measurement part 54 measures the ellipticity tan χ based on a reflected light which a light receiving part 13 receives. The measurement part 54 outputs the ellipticity tan χ to the control part 57.

The control part 57 generates a control signal based on the ellipticity tan χ inputted to the control part 57 from the measurement part 54 such that an incident light having a wavelength λ at which the ellipticity tan χ becomes zero is irradiated from the light source 52. The control part 57 outputs the control signal to the light source 52. Information inputted to the control part 57 from the measurement part 54 is not always necessary to be ellipticity tan χ per se and may be information by which the control part 57 can determine whether or not the ellipticity tan χ is zero. Information such as the phase difference δ between a p-wave and an s-wave or which wave advances a phase thereof compared to the other wave may be inputted to the control part 57 from the measurement part 54.

Figure 21:
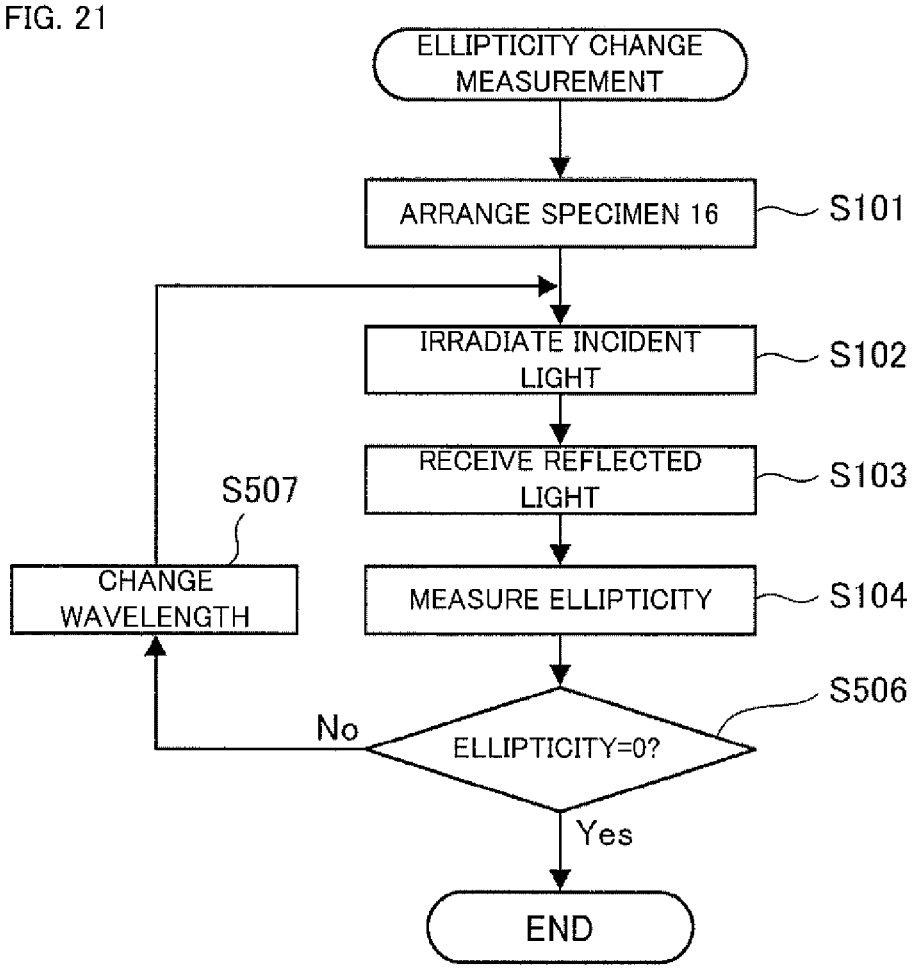
FIG. 21 is a view for explaining a method of measuring a change in the ellipticity according to the fifth embodiment of the present invention.

A method of measuring a change in the ellipticity tan χ according to this embodiment is explained in conjunction with FIG. 21. Since the processing up to step S104 is equal to the corresponding processing shown in FIG. 7, the explanation of the processing is omitted.

The measurement part 54 measures the ellipticity tan χ (step S104), and outputs the measured ellipticity tan χ to the control part 57.

When the ellipticity tan χ is not zero (no in step S506), the control part 57 generates a control signal such that a wavelength λ is changed to λ+Δλ (step S507). When the control part 57 transfers the control signal to the light source 52, the processing returns to step S102. On the other hand, when the ellipticity is zero (yes in step S506), the ellipticity change measurement is finished.

When the wavelength characteristic of a light having the ellipticity tan χ in the vicinity of the absorption wavelength λ$_0$ is formed into an approximately linear shape having the positive inclination as shown in FIG. 19, in changing a wavelength λ in step S507, the wavelength λ may be changed such that the wavelength λ is shortened when the ellipticity tan χ is positive, and the wavelength λ may be changed such that the wavelength λ is elongated when the ellipticity tan χ is negative. The wavelength characteristic of a light having the ellipticity tan χ may be formed into an approximately linear shape having the negative inclination in the vicinity of the absorption wavelength λ$_0$. In this case, the wavelength λ may be changed such that the wavelength λ is shortened when the ellipticity tan χ is negative, and the wavelength λ is elongated when the ellipticity tan χ is positive.

By changing a wavelength λ corresponding to ellipticity tan χ in this manner, the number of repeating steps in the ellipticity change measurement can be decreased.

In the surface plasmon sensor 5 according to this embodiment, firstly, the reference substance whose refractive index n$_s$ is already known is arranged on the reflection plate 11, a change in the ellipticity tan χ when the wavelength is changed is measured in accordance with steps shown in FIG. 21, and the absorption wavelength λ$_0$ at which the ellipticity tan χ becomes zero is measured.

Next, the specimen 16 whose refractive index n is to be measured is arranged on the reflection plate 11, and the absorption wavelength λ'$_0$ at which the ellipticity tan χ becomes zero is measured in accordance with steps substantially equal to the steps for measuring the refractive index n of the reference substance. In the same manner as the fourth embodiment, the refractive index n of the specimen 16 is measured based on the absorption wavelengths λ$_0$, λ'$_0$.

In the same manner as the fourth embodiment, the measurement of the refractive index n may be performed by the measurement part 54, or may be performed by the control part 57. The control part 57 may be configured to have also the function of the measurement part 54. In this case, the measurement part 54 may be omitted.

As described above, according to the surface plasmon sensor 5 of the fifth embodiment, the measurement part 54 feeds back the ellipticity tan χ and hence, the wavelength λ of the light source 52 can be changed corresponding to the measured ellipticity tan χ. Accordingly, the measurement of the absorption wavelength λ$_0$ can be performed in a short time so that a time necessary for measuring the refractive index of the specimen 16 can be shortened.

Although the wavelength λ of the light source 52 is changed corresponding to the measured ellipticity tan χ in this embodiment, the incident angle θ may be changed in place of the wavelength λ so as to measure the absorption angle θ$_0$, or the azimuth angle φ may be changed so as to measure the absorption azimuth angle φ$_0$. When the azimuth angle φ is changed, the control part 57 does not control the light source 52, but controls the reflection plate 11.

Sixth Embodiment

Figure 22:
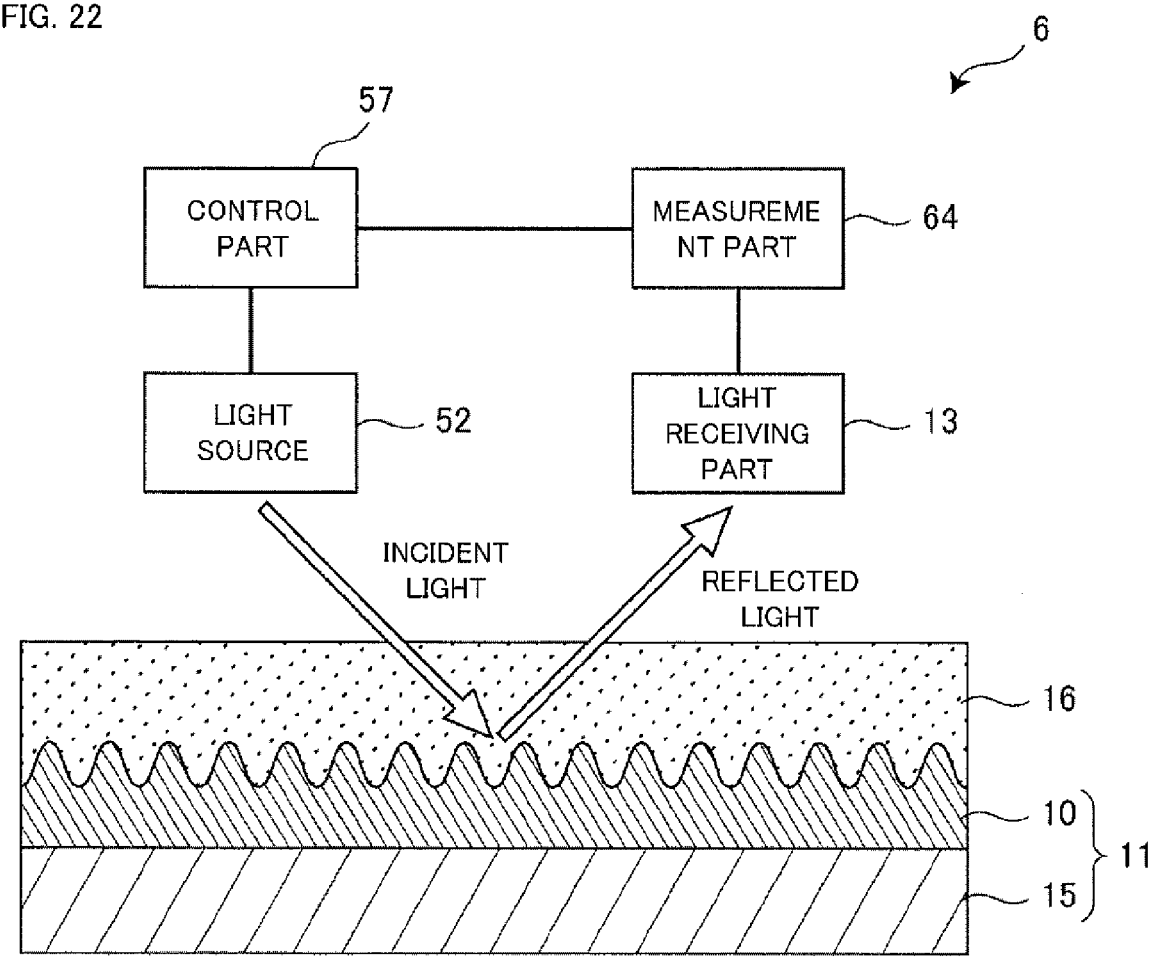
FIG. 22 is a schematic view of a surface plasmon sensor according to a sixth embodiment of the present invention.

A surface plasmon sensor 6 according to the sixth embodiment is explained in conjunction with FIG. 22.

The surface plasmon sensor 6 according to this embodiment differs from the surface plasmon sensor 5 according to the fourth embodiment with respect to a method of measuring a refractive index n using a measurement part 64. The surface plasmon sensor 6 is equal to the surface plasmon sensor 5 with respect to the constitutions other than the above-mentioned constitution and hence, the explanation of the constitutions other than the above-mentioned constitution is omitted.

Firstly, an absorption wavelength $\lambda_0$ of a reference substance is measured. The measurement of the absorption wavelength $\lambda_0$ is performed in the same manner as the measurement performed in the fifth embodiment and hence, the explanation of the measurement of the absorption wavelength $\lambda_0$ is omitted. Next, a specimen 16 whose refractive index n is to be measured is arranged on a reflection plate 11, and an incident light whose wavelength $\lambda$ is equal to an absorption wavelength $\lambda_0$ of the reference substance is irradiated from a light source 52. The measurement part 64 measures the ellipticity tan $\chi$ of reflected light which the light receiving part 13 receives.

Figure 23:
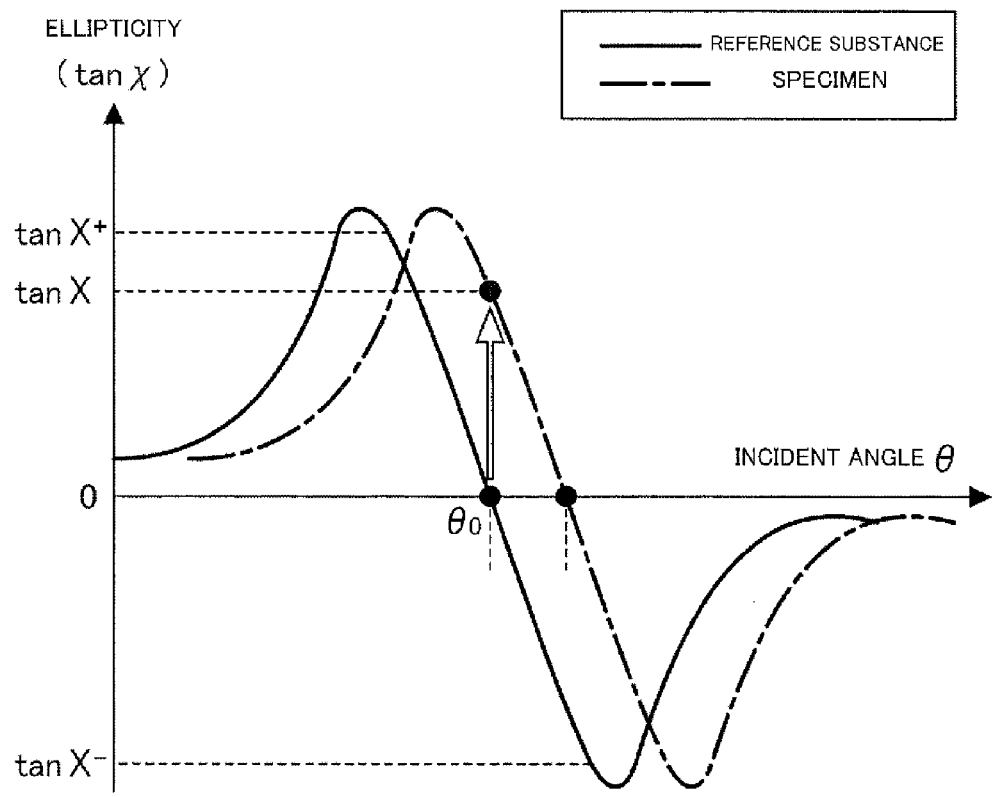
FIG. 23 is a graph showing an incident angle characteristic of a light having the ellipticity according to the sixth embodiment of the present invention.

As shown in FIG. 23, when the refractive index of the specimen 16 arranged on the reflection plate 11 is changed to $n_s+\Delta n$ from $n_s$, the incident angle characteristic of the ellipticity tan $\chi$ (the ellipticity tan $\chi$ of the reflected light being a function of the incident angle) is changed to the incident angle characteristic when the incident angle is $\theta+\Delta\theta$. Although a change $\Delta n$ in the refractive index $n_s$ may be measured by measuring a change $\Delta\theta$ in absorption angle $\theta_0$ at which the ellipticity tan $\chi$ becomes zero in the same manner as the first embodiment, a change $\Delta n$ in the refractive index $n_s$ may be measured by measuring a change in the ellipticity tan $\chi$ at a fixed wavelength $\lambda_0$ and a fixed incident angle $\theta_0$ (arrow in FIG. 23). Here, the ellipticity tan $\chi$ with respect to the specimen 16 falls within a range from tan $X^-$ to tan $X^+$ which respectively constitute a linear portion of the incident angle characteristic of the ellipticity tan $\chi$.

In this embodiment, the measurement part 64 measures a wavelength $\lambda_0$ at which the ellipticity tan $\chi$ with respect to the reference substance becomes zero at a fixed incident angle $\theta$, and measures the ellipticity tan $\chi$ with respect to the specimen 16 based on the incident angle $\theta$ and the wavelength $\lambda_0$. The measurement part 64 measures a change $\Delta n$ in the refractive index n of the specimen 16 based on the measured ellipticity tan $\chi$ with respect to the specimen 16.

In this embodiment, the wavelength $\lambda_0$ at which the ellipticity tan $\chi$ with respect to the reference substance becomes zero is measured by changing the wavelength 2 while setting the incident angle to a constant value. However, by changing the incident angle $\theta$ while setting the wavelength at a constant value, the ellipticity tan $\chi$ with respect to the specimen 16 may be measured at the incident angle $\theta_0$ and the wavelength $\lambda$ at which the ellipticity tan $\chi$ with respect to the reference substance becomes zero. Further, by changing the azimuth angle $\phi$ while setting the wavelength $\lambda$ and the incident angle $\theta$ to constant values, the ellipticity tan $\chi$ with respect to the specimen 16 may be measured at the incident angle $\theta$ and the azimuth angle $\phi_0$ at which the ellipticity tan $\chi$ with respect to the reference substance becomes zero.

As described above, in the surface plasmon sensor 6 according to this embodiment, the refractive index n of the specimen 16 is measured by making use of a change of the linear portion of the incident angle characteristic of the ellipticity tan $\chi$ brought about by a change in the refractive index of the specimen 16 and hence, it is sufficient to perform the measurement of the ellipticity of the specimen 16 only one time. Accordingly, a time necessary for the measurement can be largely shortened. Further, as shown in FIG. 23, the incident angle characteristic of the light having the ellipticity tan $\chi$ changes steeply in the vicinity of the incident angle where the ellipticity tan $\chi$ becomes zero and hence, a slight difference in the refractive index easily appears as a large change in the ellipticity tan $\chi$. Accordingly, the refractive index n of a substance such as a gas which exhibits small difference in the refractive index n, for example, can be measured with high accuracy.

Further, it is sufficient to perform the measurement of the ellipticity tan $\chi$ with respect to the specimen 16 whose refractive index n is to be measured only one time and hence, the reproducibility of the experiment is enhanced. Further, a value of tan $\chi$ varies depending on the difference between gases constituting specimens whereby the refractive index n can be measured with higher accuracy.

Seventh Embodiment

Figure 24:
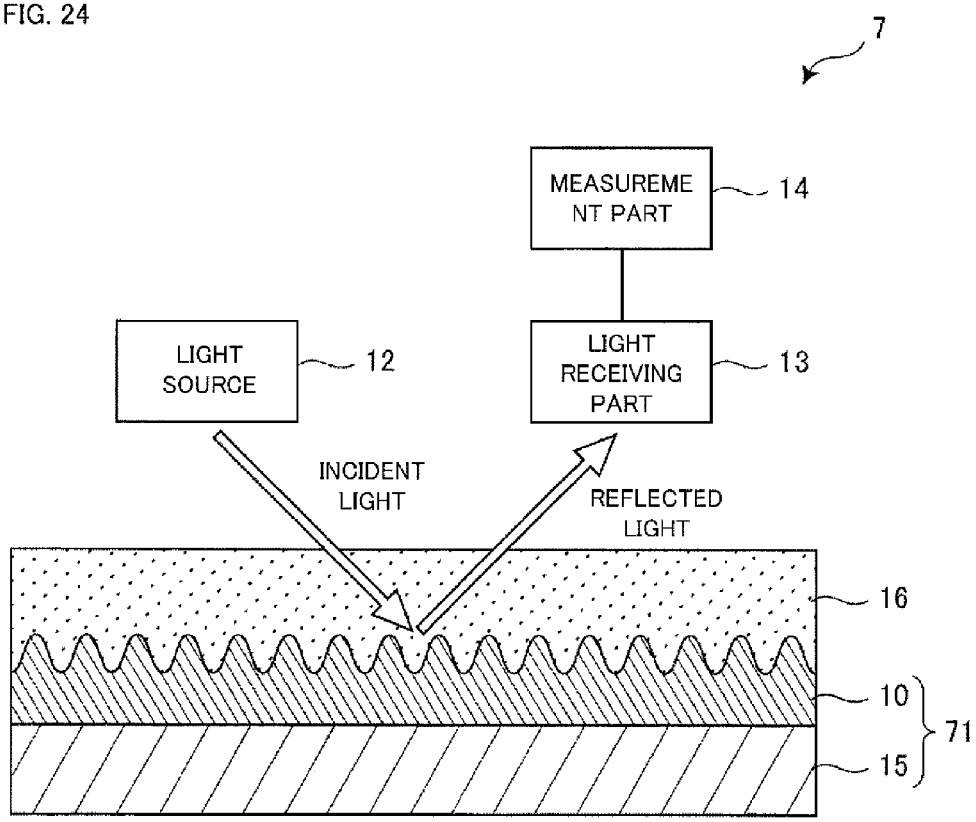
FIG. 24 is a schematic view of a surface plasmon sensor according to a seventh embodiment of the present invention.

A surface plasmon sensor 7 according to the seventh embodiment is explained in conjunction with FIG. 24.

The surface plasmon sensor 7 according to this embodiment differs from the surface plasmon sensor 1 with respect to a point that the sensitivity of measurement of the refractive index n is enhanced by adjusting a reflection plate 71. The surface plasmon sensor 7 is equal to the surface plasmon sensor 1 with respect to the constitutions other than the above-mentioned constitution and hence, the explanation of the constitutions other than the above-mentioned constitution is omitted.

Figure 25:
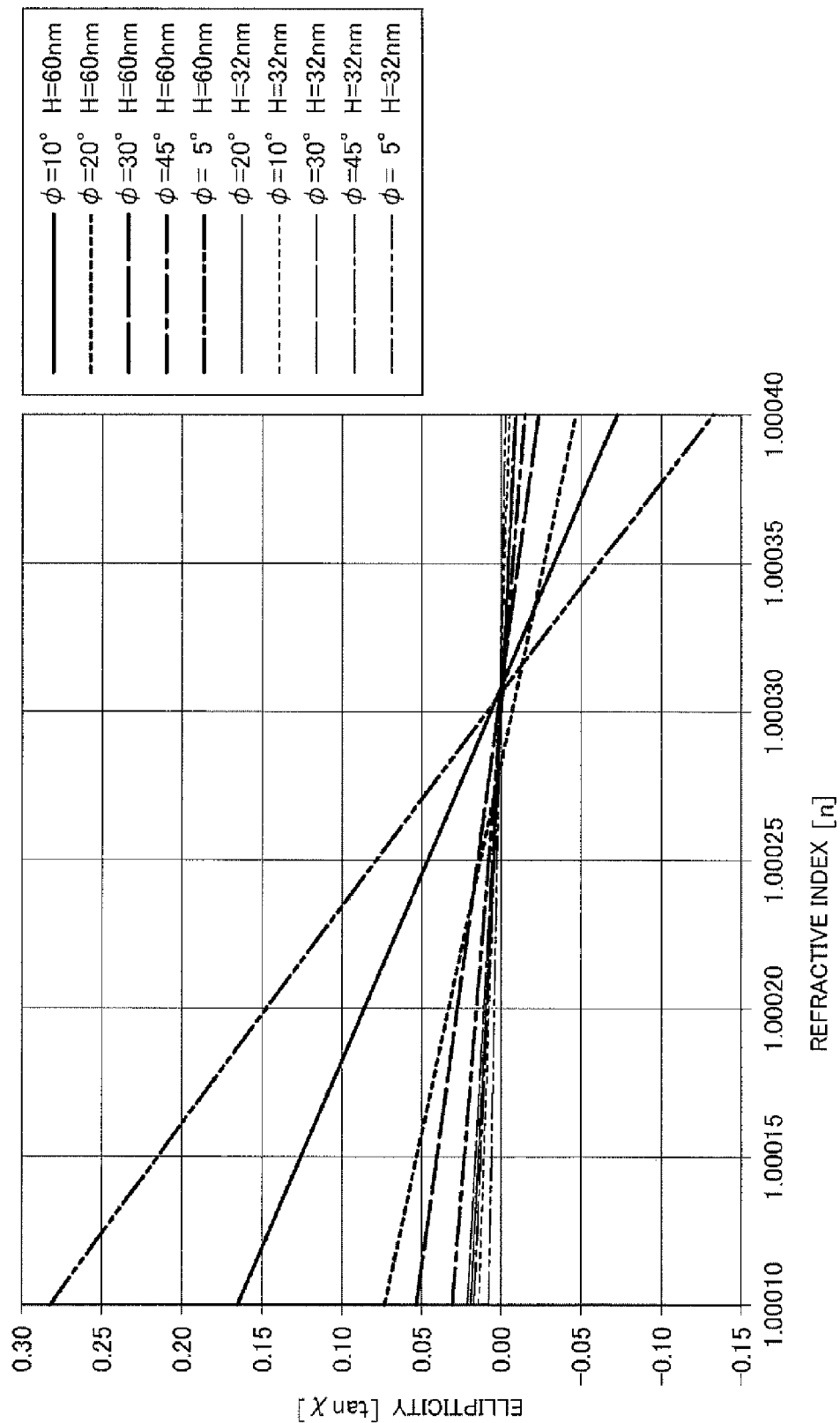
FIG. 25 is a graph showing an incident angle characteristic of a light having the ellipticity according to the seventh embodiment of the present invention.

FIG. 25 shows an incident angle characteristic of a light having the ellipticity tan $\chi$ when an azimuth angle $\phi$ of the reflection plate 71 and a shape of grooves of a grating (a depth H of the grooves in this embodiment) are changed. FIG. 25 is a graph showing a simulation result measured when air is used as a specimen 16. A method of measuring a change in the ellipticity tan $\chi$ is equal to a method shown in FIG. 7.

As shown in FIG. 25, it is understood that the inclination of the ellipticity tan $\chi$ in the vicinity of an absorption angle $\theta_0$ is changed by changing the azimuth angle $\phi$ of the reflection plate 71 and the shape of the grooves (the depth H of the grooves in this embodiment). The larger the inclination of the ellipticity tan $\chi$, the more accurately the absorption angle $\theta_0$ can be obtained. In view of the above, in the surface plasmon sensor 7 according to this embodiment, a change in the ellipticity tan $\chi$ is measured in such a manner that the inclination of the ellipticity tan $\chi$ in the vicinity of the absorption angle $\theta_0$ is set to the largest value by adjusting the azimuth angle $\phi$ of the reflection plate 71 and the shape of the grooves (the depth H of the grooves, for example).

As a method of adjusting the reflection plate 71, an incident angle characteristic of a light having the ellipticity tan $\chi$ may be measured while changing the azimuth angle $\phi$ of the reflection plate 71 and the shape of the grooves, and the azimuth angle $\phi$ of the reflection plate 71 and the shape of the grooves at which the inclination of the ellipticity tan $\chi$ in the vicinity of the absorption angle $\theta_0$ becomes the largest may be determined.

When the shape of the grooves and the azimuth angle $\phi$ are selected such that a phase difference $\delta$ between a p-wave and an s-wave of reflected light assumes $\pm 90°$ around the absorption angle $\theta_0$, and the p-wave and the s-wave have the same reflectance ($\rho_s=\rho_p$), ellipticity tan $\chi$ approximates $\pm 1$ so that the inclination of the ellipticity tan $\chi$ around the absorption angle $\theta_0$ is increased. Accordingly, the phase difference $\delta$ between the p-wave and the s-wave of reflected light or the reflectance of reflected light may be measured while changing the shape of the grooves and the azimuth angle $\phi$, and an azimuth angle $\phi$ of the reflection plate 71 and a shape of grooves at which the inclination of the ellipticity tan $\chi$ in the vicinity of the absorption angle $\theta_0$ become largest may be determined. It is sufficient to perform the adjustment of the reflection plate 71 only one time before the measurement of the refractive index n.

As described above, in the surface plasmon sensor 7 according to this embodiment, the inclination of the ellipticity tan χ in the vicinity of the absorption angle $\theta_0$ can be increased by adjusting the reflection plate 71 before the refractive index n is measured. Accordingly; the absorption angle $\theta_0$ can be measured with high accuracy so that the sensitivity of measurement of the refractive index n can be enhanced.

Although the reflection plate of the surface plasmon sensor 1 is adjusted in this embodiment, the sensitivity of measurement of the refractive index n may be enhanced by adjusting the reflection plates of the surface plasmon sensors 2, 4 to 6 in the same manner. Further, the sensitivity of measurement of the absorption angle $\theta_0$ may be enhanced by adjusting the shape of the grooves of the reflection plate of the surface plasmon sensor 3 thus increasing the inclination of the ellipticity tan χ in the vicinity of the absorption angle $\theta_0$.

Eighth Embodiment

Figure 26:
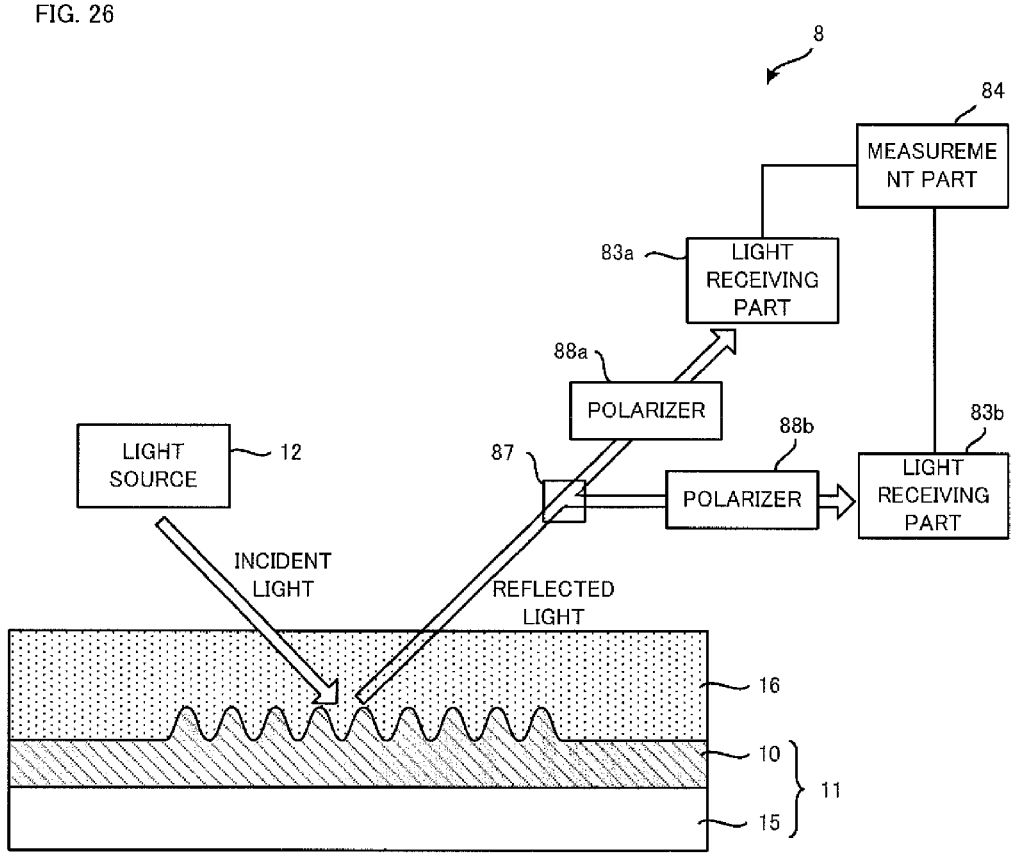
FIG. 26 is a schematic view of a surface plasmon sensor according to an eighth embodiment of the present invention.

A surface plasmon sensor 8 according to the eighth embodiment of the present invention is explained. FIG. 26 is a view showing the schematic constitution of the surface plasmon sensor 8. The surface plasmon sensor 8 according to this embodiment differs from the surface plasmon sensors according to the above-mentioned respective embodiments with respect to a point that a refractive index is measured based on phase information which constitutes a basis of the calculation of the above-mentioned ellipticity tan χ.

As explained above in conjunction with FIG. 9, a phase $\delta_p$ of a p-wave in a reflected light and a phase $\delta_s$ of an s-wave in reflected light are changed to negative from positive or to positive from negative before and after an absorption angle $\theta_0$, and a phase difference δ of reflected light is also changed to negative from positive or to positive from negative around an absorption angle $\theta_0$. In the above-mentioned embodiments, in measuring the absorption angle $\theta_0$ by making use of such a characteristic, an angle of incidence at which the phase difference δ becomes zero is specified as an absorption angle $\theta_0$ by measuring the ellipticity tan χ.

To the contrary, in the eighth embodiment, a value corresponding to a phase difference δ between a p-wave of reflected light and an s-wave of reflected light is measured using a polarizer, and an angle of incidence at which the phase difference δ becomes zero (absorption angle $\theta_0$) can be measured. Accordingly, an absorption angle $\theta_0$ can be specified and, eventually, the refractive index n can be specified without measuring the ellipticity tan χ. That is, equipment such as a polarimeter for measuring an ellipticity tan χ becomes unnecessary.

As shown in FIG. 26, the surface plasmon sensor 8 includes a splitter 87, polarizers 88a, 88b, and two light receiving parts 83a, 83b. The surface plasmon sensor 8 is substantially equal to the surface plasmon sensor 1 shown in FIG. 1 with respect to the constitutions other than the above-mentioned constitution and hence, the explanation of the constitutions other than the above-mentioned constitution is omitted.

The splitter 87 is arranged on a path of a reflected light reflected on a reflection plate 11, splits an optical flux of reflected light into two, and makes one optical flux incident on the light receiving part 83a and makes the other optical flux incident on the light receiving part 83b.

The polarizer 88a is arranged on a path of one split optical flux which is generated by the splitter 87, and selectively allows a component polarized in the specific direction in the optical flux to pass therethrough. The polarizer 88b is arranged on a path of the other split optical flux which is generated by the splitter 87, and selectively allows a component polarized in the specific direction in the optical flux which to pass therethrough. Due to such a constitution, the light receiving parts 83a, 83b receive reflected lights which are polarized in the specific directions respectively.

The polarizer 88a and the polarizer 88b have the directions of transmission axes thereof adjusted such that components which are polarized in different directions to pass through the polarizer 88a and the polarizer 88b respectively. For example, in embodiments described later in conjunction with FIG. 28 and FIG. 30, the polarizer 88a is adjusted such that a light which is polarized in the same direction as an inclination angle φ of an ellipse of reflected light is selectively made to pass through the polarizer 88a, and the polarizer 88b is adjusted such that a light which is polarized in the direction orthogonal to the inclination angle φ of the ellipse of reflected light is selectively made to pass through the polarizer 88b. In this manner, by making the lights which differ from each other in the inclination angle of the ellipse by 90° selectively pass through the respective polarizers, the increase or the decrease of the phase difference δ of reflected light can be measured.

In other words, it is sufficient that at least one of the polarizers 88a, 88b is adjusted such that a portion of the light which is polarized in the direction orthogonal to the direction of the inclination angle φ of the ellipse of reflected light id made to pass through the polarizer. Due to such a constitution, at least one of the light receiving parts measures a tendency of the increase or the decrease of the phase difference δ of reflected light so that the measurement part 84 can measure the absorption angle $\theta_0$ at which the phase difference δ becomes zero.

The measurement part 84 measures changes in intensity of reflected lights which the light receiving parts 83a, 83b receive through the polarizers 88a, 88b respectively. Then, the measurement part 84 can measure the absorption angle $\theta_0$ based on the changes in intensity of reflected lights.

A method of measuring an absorption angle $\theta_0$ according to this embodiment is explained.

Figure 27:
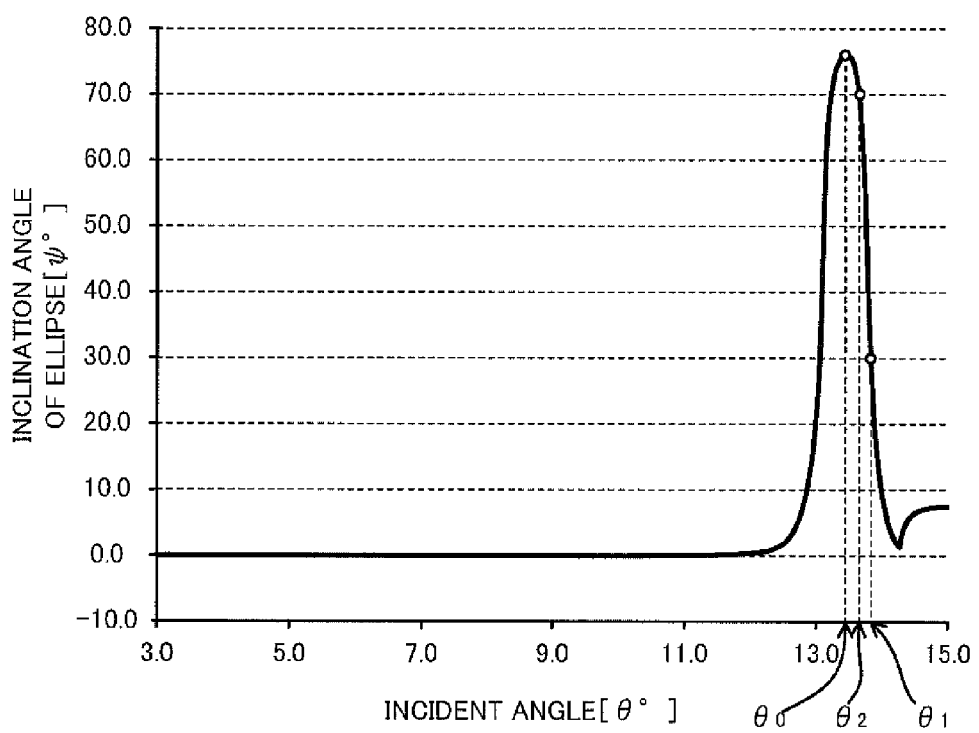
FIG. 27 is a graph showing an angle of incidence—an inclination angle characteristic of an ellipse according to the eighth embodiment of the present invention.

FIG. 27 is a graph showing the relationship between an angle of incidence θ and an inclination angle φ of an ellipse. FIG. 27 shows a simulation result of a change in the inclination angle φ of the ellipse at respective incident angles θ. Here, a holographic aluminum grating is used as the reflection plate 11. A depth H of grooves of the grating is set to 72 nm (H=72 nm), a period d of the grating is set to 556=(d=556 nm), an azimuth angle φ is set to 30° (φ=30°), a wavelength λ is set to 670=(λ=670 nm), and an angle of incidence θ is changed within a range of 3°<θ<15°. As shown in the drawing, the inclination angle φ of the ellipse has a peak thereof around the absorption angle $\theta_0$.

In FIG. 27, $\theta_1$ indicates an angle of incidence at which an inclination angle φ of the ellipse is 30° (φ=30°), and $\theta_2$ indicates an angle of incidence at which an inclination angle φ of the ellipse is 70° (φ=70°. Although the incident angles $\theta_1$, $\theta_2$ are offset from the absorption angle $\theta_0$, the incident angles $\theta_1$, $\theta_2$ fall within a range of several degrees from the absorption angle $\theta_0$.

Figure 28:
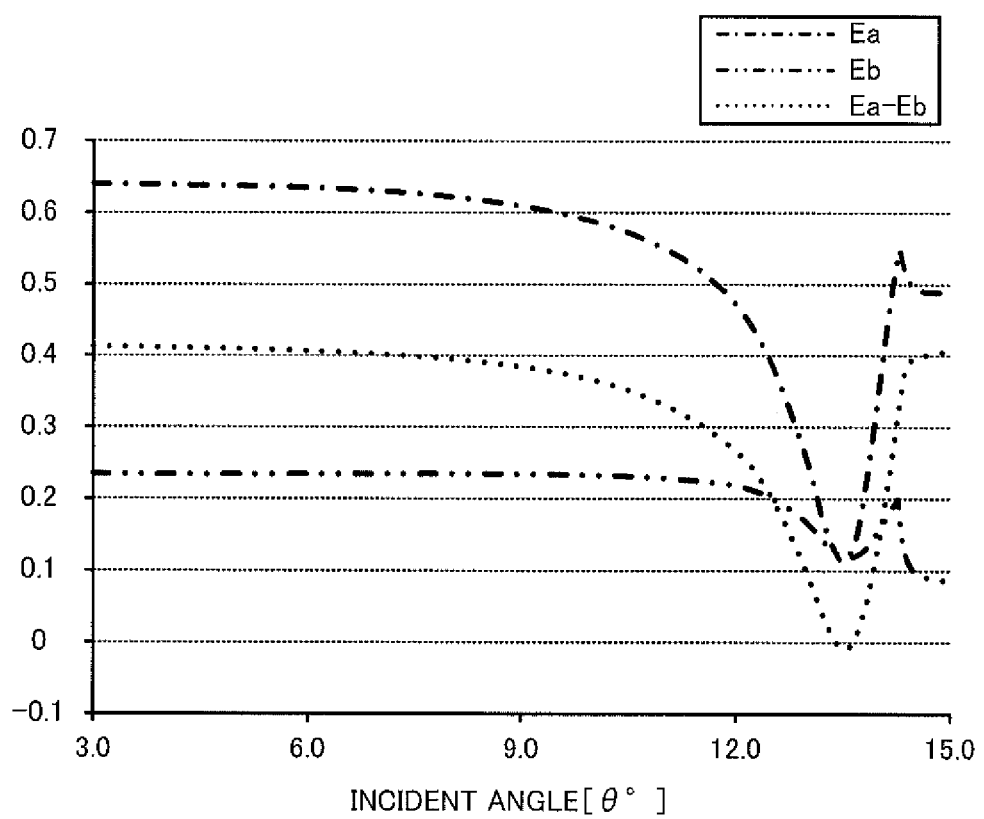
FIG. 28 is a graph showing a received light intensity characteristic according to the eighth embodiment of the present invention.

FIG. 28 is a graph showing a simulation result of the intensity of received light measured by the measurement part 84 under a condition that the inclination angle φ of the ellipse of the incident light is set to 30°. Here, a holographic aluminum grating is used as the reflection plate 11. A depth H of grooves of the grating is set to 72 nm (H=72 nm), a period d of the grating is set to 556 nm (d=556 nm), an azimuth angle φ is set to 30° (φ=30°), a wavelength λ is set to 670 nm (λ=670 nm), and an angle of incidence θ is changed within a range of 3°<θ<15°. In the drawing, the intensity of received light Ea of the light receiving part 83a is indicated by a chained line, the intensity of received light Eb of the light receiving part 83b is indicated by a double-dashed chained line, and the difference Ea–Eb between the intensities of the received lights is indicated by a dotted line.

The intensities of received lights Ea, Eb and the difference Ea–Eb change linearly within a predetermined range around the incident angle $\theta_1$. Accordingly, by measuring or simulating a linear change within the predetermined range using a reference specimen, and by using a measurement result or a simulation result as calibration data, it is possible to measure a change in the incident angle $\theta_1$ brought about by a change in the refractive index n.

Figure 29:
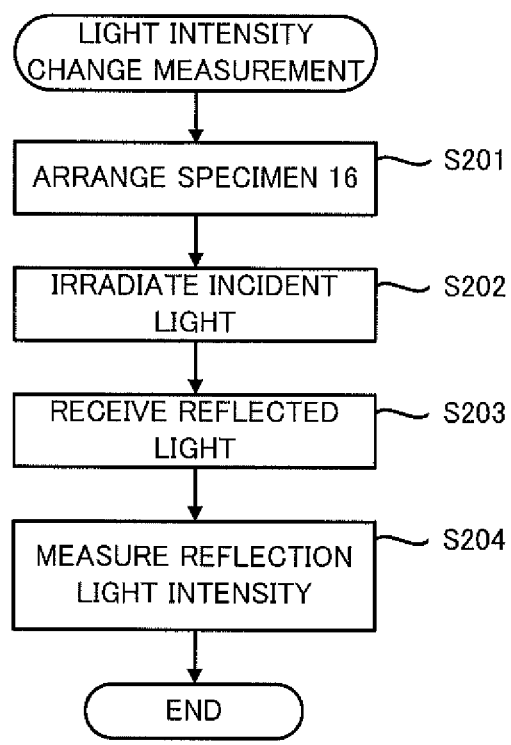
FIG. 29 is a view for explaining a method of measuring intensity of a received light according to the eighth embodiment of the present invention.

FIG. 29 is a flowchart showing steps of measuring a refractive index n according to this embodiment. In the measuring method shown in the flowchart, a change in intensity of a reflected light from the specimen 16 (hereinafter referred to as reflected light intensity I) when the specimen 16 is arranged on the reflection plate 11 is measured.

Firstly, the specimen 16 is arranged on the reflection plate 11 (S201), and an incident light having an angle of incidence $\theta$ and a wavelength $\lambda$ is irradiated from the light source 12 (S202). Here, the light source 12 irradiates an incident light of a p-wave. An angle of incidence $\theta$ of the incident light takes a value within a predetermined range around the above-mentioned incident angle $\theta_1$.

The light receiving parts 83a, 83b receive a reflected light which is obtained by the reflection of the incident light on the reflection plate 11 through the specimen 16 (S203).

The measurement part 84 measures reflected light intensity I based on reflected light (S204).

Based on reflected light intensity I measured in such a manner, the measurement part 84 specifies a change amount $\Delta I$ of reflected light intensity I from calibration data while referencing the above-mentioned calibration data. The measurement part 84 measures the difference $\Delta n(=n-n_s)$ between a refractive index $n_s$ of the reference substance and a refractive index of the specimen 16 based on the change amount $\Delta I$.

Figure 30:
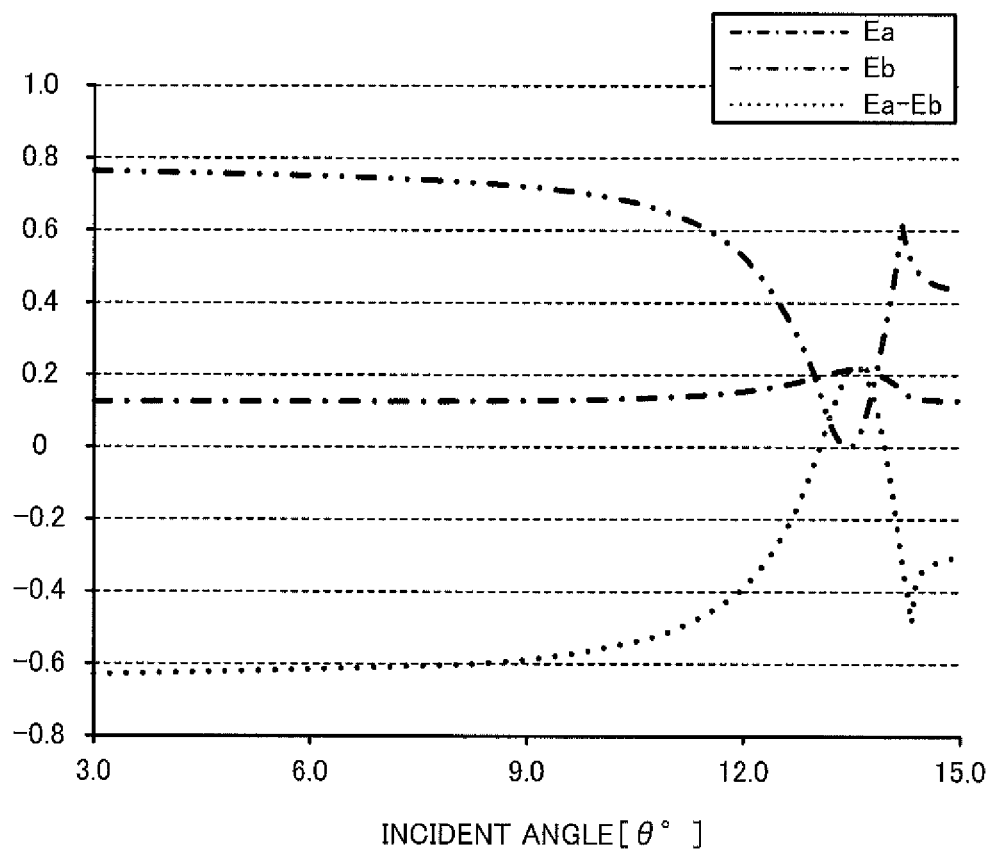
FIG. 30 is a graph showing a received light intensity characteristic according to the eighth embodiment of the present invention.

The inclination angle $\phi$ of the ellipse of the incident light is not limited to 30°, and can be set to various values within a range of angle which the inclination angle $\phi$ of the ellipse can take. For example, FIG. 30 is a graph showing a simulation result of the intensity of a received light measured by the measurement part 84 under a condition that the inclination angle $\phi$ of the ellipse of the incident light is set to 70°. Here, a holographic aluminum grating is used as the reflection plate 11. A depth H of grooves of the grating is set to 72 nm (H=72 nm), a period d of the grating is set to 556 nm (d=556 nm), an azimuth angle $\phi$ is set to 30° ($\phi$=30°), a wavelength $\lambda$ is set to 670 nm ($\lambda$=670 nm), and an angle of incidence $\theta$ is changed within a range of 3°<$\theta$<15°.

In FIG. 30, the intensity of received light Ea of the light receiving part 83a is indicated by a chained line, the intensity of received light Eb of the light receiving part 83b is indicated by a double-dashed chained line, and the difference Ea–Eb between the intensities of the received lights is indicated by a dotted line. Also in FIG. 30, the intensities of received lights Ea, Eb and the difference Ea–Eb change linearly within a predetermined range around the incident angle $\theta_2$ and hence, a change in the incident angle $\theta_2$ can be measured using calibration data within such a predetermined range.

As described above, the surface plasmon sensor 8 according to the eighth embodiment can measure the refractive index n using a value corresponding to the phase difference $\delta$ which is obtained using the polarizer. That is, the measurement of ellipticity tan $\chi$ is unnecessary and hence, a refractive index n can be measured without using expensive and complex equipment for measuring ellipticity tan $\chi$ such as a polarimeter.

Ninth Embodiment

Figure 31:
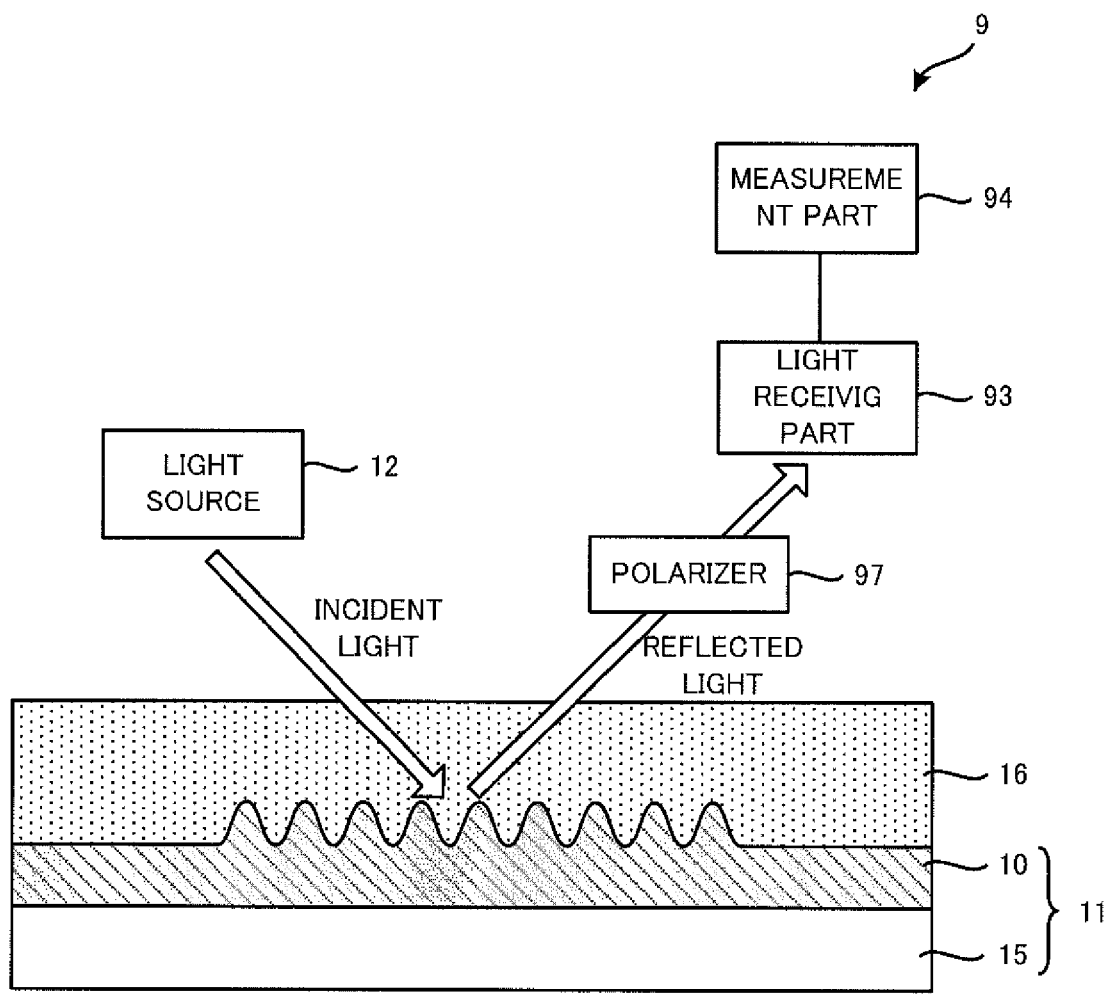
FIG. 31 is a schematic view of a surface plasmon sensor according to a ninth embodiment of the present invention.

A surface plasmon sensor 9 according to the ninth embodiment of the present invention is explained. FIG. 31 is a view showing the schematic constitution of the surface plasmon sensor 9. The surface plasmon sensor 9 according to this embodiment differs from the above-mentioned surface plasmon sensor 8 according to the eighth embodiment with respect to a point that the surface plasmon sensor 9 does not include the splitter but includes one polarizer and one light receiving part.

As shown in FIG. 31, the surface plasmon sensor 9 includes a polarizer 98 and a light receiving part 93. The polarizer 98 is arranged on a path of a reflected light, and allows a component polarized in the specific direction in reflected light to selectively pass therethrough. Due to such a constitution, the polarizer 98 receives reflected light polarized in the specific direction by the polarizer 98.

A measurement part 94 can measure a change in intensity of a reflected light which the light receiving part 93 receives through the polarizer 98. The measurement part 94 can measure an angle of incidence (absorption angle $\theta_0$) based on a change in intensity of reflected light. The surface plasmon sensor 9 is substantially equal the surface plasmon sensor 8 shown in FIG. 26 with respect to the constitutions other than the above-mentioned constitution and hence, the explanation of the constitutions other than the above-mentioned constitution is omitted. Further, a method of measuring a refractive index n is also substantially equal to the method of measuring the refractive index based on the intensities of received lights Ea, Eb explained in the eighth embodiment and hence, the explanation of method of measuring the refractive index n is omitted.

As described above, the surface plasmon sensor 9 according to the ninth embodiment can measure the refractive index n by acquiring a value corresponding to the phase difference $\delta$ using one set of the polarizer and the light receiving part.

The reflection plates of the surface plasmon sensors 3 to 9 according to the third to ninth embodiments may be configured such that an incident light is incident on the reflection plate from a substrate 25 side in the same manner as the second embodiment.

In the first to seventh embodiments, as in the case of the eighth and ninth embodiments, a refractive index n can be measured using an absorption angle $\theta_0$ or an absorption azimuth angle $\phi_0$ which is measured by measuring a value corresponding to the phase difference $\delta$ of reflected light using the polarizer, or an absorption wavelength $\lambda_0$ in place of using the ellipticity tan $\chi$.

Finally, the above-mentioned explanation of the respective embodiments merely illustrates one example of the present invention, and the present invention is not limited to the above-mentioned embodiments. Accordingly, it is needless to say that various modifications are conceivable besides the above-mentioned respective embodiments depending on designs and the like without departing from the technical concept of the present invention.

DESCRIPTION OF REFERENCE NUMERALS AND SIGNS 11, 21, 31, 71: reflection plate, 12, 42, 52: light source, 13, 83a, 83b: light receiving part, 14, 34, 44, 54, 64, 84, 94: measurement part, 57: control part, 87: splitter, polarizer: 88a, 88b

The invention claimed is:

1. A surface plasmon sensor comprising:
a reflection plate which includes a metal layer having a periodic structure and on which a specimen is arranged;
a light source which irradiates an incident light of a p polarized light or an s polarized light to the reflection plate arranged in a conical mount;
a light receiving part which receives a reflected light reflected on the reflection plate; and
a measurement part which measures a refractive index of the specimen based on a parameter by which ellipticity of the reflected light becomes zero by changing any one of an incident angle of the incident light which the light source irradiates to the reflection plate, an azimuth angle which the plane of incidence makes with respect to the periodic direction of the periodic structure, and a wavelength of the incident light which is incident from the light source as the parameter.

2. The surface plasmon sensor according to claim 1, wherein
the surface plasmon sensor further comprises a control part which controls the reflection plate for changing the parameter such that the ellipticity measured by the measurement part becomes zero.

3. The surface plasmon sensor according to claim 1, wherein
the light source irradiates to the specimen the incident light having an incident angle, an azimuth angle and a wavelength at which ellipticity in a state where a reference substance which constitutes a reference in measuring a refractive index is arranged on a reflection plate becomes zero, and
the measurement part measures a refractive index of the specimen based on the ellipticity obtained from the reflected light.

4. The surface plasmon sensor according to claim 1, wherein a shape of grooves formed in a grating relative to the incident light is changed by adjusting an azimuth angle of the reflection plate such that a change amount of the ellipticity before and after a point where the ellipticity becomes zero is large.

5. The surface plasmon sensor according to claim 1, wherein a shape of grooves of a grating relative to the incident light is changed by adjusting an azimuth angle of the reflection plate such that the phase difference between a component of the reflected light parallel to the plane of incidence and a component of the reflected light perpendicular to the plane of incidence is set approximately perpendicular, and reflectance of the reflected light becomes substantially equal between the component of the reflected light parallel to the plane of incidence and the component of the reflected light perpendicular to the plane of incidence.

6. The surface plasmon sensor according to claim 1, wherein
the light source irradiates the incident light such that the incident light is incident on a surface of the reflection plate opposite to a surface of the reflection plate on which the metal layer is formed, and
the metal layer has a thin film periodic structure.

7. The surface plasmon sensor according to claim 1, wherein
the reflection plate includes a substrate which allows a light to pass therethrough, and a metal layer which is laminated to one surface of the substrate and has a periodic structure,
a specimen is arranged on a surface of the metal layer which is not brought into contact with the substrate,
the light source irradiates an incident light from a side of the other surface of the substrate, and
the light receiving portion receives a reflected light reflected on the side of the other surface of the substrate.

8. A method of measuring a refractive index using a surface plasmon sensor which measures a refractive index of a specimen arranged on a reflection plate provided with a metal layer having a periodic structure, wherein
the method comprising the steps of:
irradiating an incident light of a p polarized light or an s polarized light to the reflection plate arranged in a conical mount from a light source;
receiving a reflected light which passes through the specimen and is reflected on the reflection plate by a light receiving part; and
measuring a refractive index of the specimen based on a parameter by which ellipticity of the reflected light becomes zero by changing any one of an incident angle of the incident light which the light source irradiates to the reflection plate, an azimuth angle which the plane of incidence makes with respect to the periodic direction of the periodic structure, and a wavelength of the incident light which is incident from the light source as the parameter.

9. A surface plasmon sensor comprising:
a reflection plate which includes a substrate which allows a light to pass therethrough, and a metal layer which is laminated to one surface of the substrate and has a thin film periodic structure, a specimen being arranged on a surface of the metal layer which is not brought into contact with the substrate;
a light source which irradiates an incident light from a side of the other surface of the substrate;
a light receiving part which receives a reflected light reflected on the other surface of the substrate;
a measurement part which measures a refractive index of the specimen based on a parameter by which ellipticity of the reflected light becomes zero by changing any one of an incident angle of the incident light which the light source irradiates to the reflection plate, an azimuth angle which the plane of incidence makes with respect to the periodic direction of the periodic structure, and a wavelength of the incident light which is incident from the light source as the parameter; and
a control part which controls the reflection plate so as to change the parameter such that the ellipticity measured by the measurement part becomes zero, wherein
a shape of grooves of a grating relative to the incident light is changed by adjusting an azimuth angle of the reflection plate such that the phase difference between a component of the reflected light parallel to the plane of incidence and a component of the reflected light perpendicular to the plane of incidence is set approximately perpendicular, and reflectance of the reflected light becomes substantially equal between the component of the reflected light parallel to the plane of incidence and the component of the reflected light perpendicular to the plane of incidence, and
the measurement part sets as a refractive index of the specimen a value corresponding to ellipticity of a reflected light which the light receiving part receives in a state where a wavelength, an incident angle and an azimuth angle are fixed to values at which the ellipticity of the reflected light when a reference substance whose refractive index is known is arranged on the reflection plate as the specimen becomes zero.

10. A surface plasmon sensor comprising:
a reflection plate which includes a metal layer having a periodic structure and on which a specimen is arranged;
a light source which irradiates an incident light to the reflection plate;
a splitter which splits a reflected light reflected on the reflection plate into two optical fluxes;
a first light receiving portion which receives one optical flux formed by splitting by the splitter;
a second light receiving portion which receives the other optical flux formed by splitting by the splitter;
a first polarizer which is arranged on a path of said one optical flux formed by splitting by the splitter;
a second polarizer which is arranged on a path of said the other optical flux formed by splitting by the splitter; and
a measurement part which sets as a refractive index of a substance to be measured whose refractive index is not known a value corresponding to a difference between a difference between intensity of received light of the first light receiving part and intensity of received light of the second light receiving part when a reference substance whose refractive index is already known is arranged on the reflection plate as the specimen and a difference between intensity of received light of the first light receiving part and intensity of received light of the second light receiving part when the substance to be measured whose refractive index is not known is arranged on the reflection plate as the specimen, wherein an azimuth angle of the reflection plate is adjusted such that the phase difference between a component of the reflected light parallel to the plane of incidence and a component of the reflected light perpendicular to the plane of incidence is set approximately perpendicular, and reflectance of the reflected light becomes substantially equal between the component of the reflected light parallel to the plane of incidence and the component of the reflected light perpendicular to the plane of incidence, the first polarizer is adjusted so as to selectively make a light polarized in the same direction as an inclination angle of an ellipse which a field vector of the reflected light forms pass therethrough, and the second polarizer is adjusted so as to selectively make a light polarized in the direction orthogonal to the inclination angle of the ellipse which the field vector of the reflected light forms pass therethrough.

* * * * *